United States Patent
Camilli et al.

(10) Patent No.: US 10,953,053 B2
(45) Date of Patent: Mar. 23, 2021

(54) **METHODS AND COMPOSITIONS FOR PREVENTING INFECTION BY A *VIBRIO* SPECIES**

(71) Applicant: Trustees of Tufts College, Medford, MA (US)

(72) Inventors: Andrew Camilli, Sharon, MA (US); Lynne Cairns, Somerville, MA (US); Minmin Yen, Cambridge, MA (US)

(73) Assignee: TRUSTEES OF TUFTS COLLEGE, Medford, MA (US)

( * ) Notice: Subject to any disclaimer, the term of this patent is extended or adjusted under 35 U.S.C. 154(b) by 50 days.

(21) Appl. No.: 16/145,836

(22) Filed: Sep. 28, 2018

(65) Prior Publication Data
US 2019/0099459 A1    Apr. 4, 2019

Related U.S. Application Data

(63) Continuation of application No. PCT/US2017/025305, filed on Mar. 31, 2017.

(60) Provisional application No. 62/316,704, filed on Apr. 1, 2016.

(51) Int. Cl.
| | |
|---|---|
| *A61K 35/76* | (2015.01) |
| *C12N 7/00* | (2006.01) |
| *C12N 7/02* | (2006.01) |
| *A61P 31/04* | (2006.01) |
| *A61K 9/00* | (2006.01) |
| *A61K 45/06* | (2006.01) |

(52) U.S. Cl.
CPC ............ *A61K 35/76* (2013.01); *A61K 9/0053* (2013.01); *A61K 45/06* (2013.01); *A61P 31/04* (2018.01); *C12N 7/00* (2013.01); *C12N 7/02* (2013.01); *C12N 2795/00021* (2013.01); *C12N 2795/00032* (2013.01); *Y02A 50/30* (2018.01)

(58) Field of Classification Search
None
See application file for complete search history.

(56) References Cited

U.S. PATENT DOCUMENTS

| 5,766,892 A | 6/1998 | Merril et al. |
| 8,003,323 B2 | 8/2011 | Morris et al. |
| 2014/0105866 A1 | 4/2014 | Espejo Torres et al. |
| 2015/0064138 A1 | 3/2015 | Lu et al. |
| 2015/0297648 A1 | 10/2015 | Deaton et al. |

OTHER PUBLICATIONS

Jaiswal et al. "Efficacy of coctail phage therapy in treating Vibrio cholerae infeciton in rabiit model". Microbes and Infection 2013, 15, pp. 152-156.*

Abel, S et al. Infant Rabbit Model for Diarrheal Diseases. Current protocols in microbiology 38, 6A 6 1-15 (2015).

Butler, SM et al. Cholera stool bacteria repress chemotaxis to increase infectivity. Mol Microbiol 60 (2), 417-26 (2006). PMCID: PMC2754204.

Chatterjee, SN et al. Lipopolysaccharides of Vibrio cholerae: II. Genetics of biosynthesis. Biochimica et biophysica acta 1690, 93-109 (2004).

D'Herelle, F et al. A Preliminary report of work carried out by the cholera bacteriophage enquiry. Ind. Med. Gaz. 62:614-616 (1927). (Note that this paper is not available on PubMed, but the data are restated in a review by d'Herelle, PMID: 21433426.

Dutta, NK et al. An Experimental Study on the Usefulness of Bacteriophage in the Prophylaxis and Treatment of Cholera. Bull. Wld Hlth Org. 28, 357-360 (1963).

Faruque, SM et al. Seasonal epidemics of cholera inversely correlate with the prevalence of environmental cholera phages. Proc. Natl Acad. Sci. USA 102, 1702-1707 (2005).

Faruque, SM et al. Self-limiting nature of seasonal cholera epidemics: role of host-mediated amplification of phage. Proc. Natl Acad. Sci. USA 102, 6119-6124 (2005).

Fu, Y et al. Tn-Seq analysis of Vibrio cholerae intestinal colonization reveals a role for T6SS-mediated antibacterial activity in the host. Cell host & microbe 14, 652-663, 2013.

Harris, JB et al. Susceptibility to Vibrio cholerae, Infection in a cohort of household contacts of patients with cholera in Bangladesh. PLoS Negl. Trop. Dis. 2,e221 (2008).

Heidelberg, JF et al. DNA sequence of both chromosomes of the cholera pathogen *Vibrio cholerae*. Nature 406, 477-483, 2000.

Jensen, MA et al. Modeling the role of bacteriophage in the control of cholera outbreaks. Proc. Natl Acad. Sci. USA 103, 4652-4657 (2006).

Kamp, HD et al. Gene Fitness Landscapes of Vibrio cholerae at Important Stages of Its Life Cycle. PLoS Pathog. 9 (12):e1003800 (2013). PMCID: PMC3873450.

Lazinski, DW et al. Homopolymer tail-mediated ligation PCR: a streamlined and highly efficient method for DNA cloning and library construction. BioTechniques 54, 25-34 (2013).

Luquero, FJ et al. Mortality Rates during Cholera Epidemic, Haiti, 2010-2011. Emerging infectious diseases 22, 410-416 (2016).

(Continued)

*Primary Examiner* — Vera Afremova
(74) *Attorney, Agent, or Firm* — Nixon Peabody LLP; David S. Resnick; Nicole D. Kling

(57) ABSTRACT

Compositions and methods are provided for preventing, ameliorating, or treating a disease caused by a species of bacterial genus *Vibrio*, for example, cholera caused by *V. cholerae*, the compositions containing two or more strains of lytic bacteriophage that infect and kill *Vibrio* cells. The bacteriophage are virulent, which replicate intracellularly and lyse and kill the bacteria. Use of two or more strains in a single treatment, as a result of a rate of mutation of the bacteria to simultaneous resistance to all of the bacteriophage to be so low as to be negligible, reduces appearance of phage-resistant bacteria to statistical negligibility. Normal human microbial flora species were not affected. In alternative embodiments of the method and the composition, antibiotic agents or other treatment agents can be administered with a cocktail of the plurality of bacteriophage strains.

12 Claims, 9 Drawing Sheets

(56) References Cited

OTHER PUBLICATIONS

Ly-Chatain, MH. The factors affecting effectiveness of treatment in phages therapy. Front Microbiol. 5:51, 1-7 (2014).
Ma, Y et al. Microencapsulation of bacteriophage felix O1 into chitosan-alginate microspheres for oral deliveryApp. Environ. Micro. 74 (15): 4799-4805 (2008).
Nelson, EJ et al. Complexity of rice-water stool from patients with Vibrio cholerae plays a role in the transmission of infectious diarrhoea. Proc. Natl Acad. Sci. USA 104, 19091-19096 (2007). PMCID: PMC2141913.
Nelson, EJ et al. Transmission of Vibrio cholerae is antagonized by lytic phage and entry into the aquatic environment. PLoS Pathog. 4, e1000187 (2008). PMCID: PMC2563029.
Nelson, EJ et al. Cholera transmission: the host, pathogen and bacteriophage dynamic. Nat Rev Microbiol. Oct;7 (10):693-702. Review (2009). PMID: 19756008.
Pasricha, CL et al. Season variations of cholera bacteriophage in natural waters and in man in Calcutta during the year 1930. Ind. Med. Gaz. 66, 543-550 (1931).
Pritchard, Jr et al. Artist: high-resolution genome-wide assessment of fitness using transposon-insertion sequencing. PLoS genetics 10, e1004782 (2014).
Qadri, F et al. Efficacy of a Single-Dose, Inactivated Oral Cholera Vaccine in Bangladesh. The New England journal of medicine 374, 1723-1732 (2016).
Reveiz, L et al. Chemoprophylaxis in contacts of patients with cholera: systematic review and meta-analysis. PloS one 6, e27060 (2011).
Seed, KD et al. Evidence of a Dominant Lineage of Vibrio cholerae-Specific Lytic Bacteriophages Shed by Cholera Patients over a 10-Year Period in Dhaka, Bangladesh. MBio. 2(1). pii: e00334-10 (2011). PMCID: PMC3037004.
Seed, KD et al. Phase Variable O Antigen Biosynthetic Genes Control Expression of the Major Protective Antigen and Bacteriophage Receptor in Vibrio cholerae O1. PLoS Pathog. 8(9):e1002917 (2012). PMCID: PMC3441752.
Seed, KD et al. A bacteriophage encodes its own CRISPR/Cas adaptive response to evade host innate immunity. Nature. 494(7438):489-91 (2013). PMCID: PMC3587790.
Seed, KS et al. Evolutionary Consequences of Intra-Patient Phage Predation on Microbial Populations. eLife (2014). 3:e03497. PMID: 25161196.
Tamayo, R et al. Growth in a biofilm induces a hyperinfectious phenotype in Vibrio cholerae. Infect Immun. 78(8)3560-9 (2010). PMCID: PMC2916270.
Taylor, DL et al. The Impact of Water, Sanitation and Hygiene Interventions to Control Cholera: A Systematic Review. PloS one 10, e0135676 (2015).
Weil, AA et al. Clinical outcomes in household contacts of patients with cholera in Bangladesh. Clin Infect Dis. 15;49(10):1473-9 (2009).
Wittebole, X et al. A historical overview of bacteriophage therapy as an alternative to antibiotics for the treatment of bacterial pathogens. Virulence 5, 226-235 (2014).
Zahid, MS et al. Effect of phage on the infectivity of Vibrio cholerae and emergence of genetic variants. Infect Immun 76: 5266-5273 (2008).
Zuckerman, JN et al. The true burden and risk of cholera: implications for prevention and control. The Lancet Infectious Diseases 7, 521-530 (2007).
Bagcchi, S. Cholera in Iraq strains the fragile state. The Lancet Infectious Diseases 16, 24-25, 2016.
Hava, DL et al. Isolation and characterization of a temperature-sensitive generalized transducing bacteriophage for Vibrio cholerae. J.Micr.Methods, 46: 217-225 (2001).
Jaiswal, A et al. Comparative analysis of different oral approaches to treat Vibrio cholerae infection in adult mice. International Journal of Medical Microbiology 304, 422-430 (2014).
Jaiswal, A et al. Efficacy of cocktail phage therapy in treating Vibrio cholerae infection in rabbit model. Microbes and Infection 15, 152-156 (2013).
International Search Report and Written Opinion of the International Search Authority in PCT/US17/25305 dated Aug. 2, 2017 (15 pgs.).

* cited by examiner

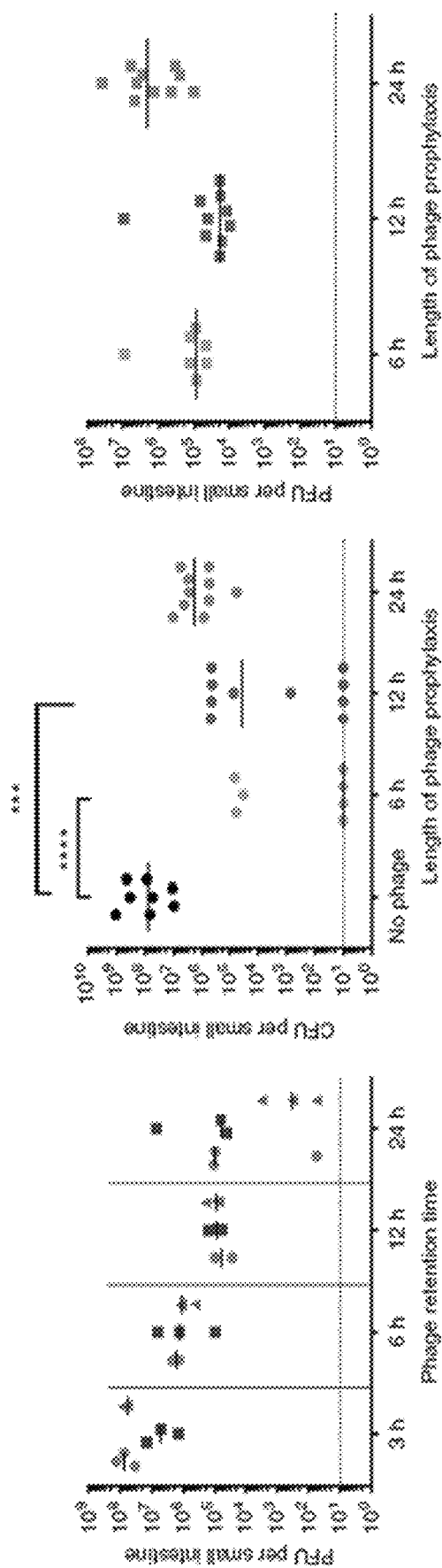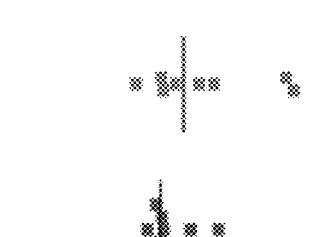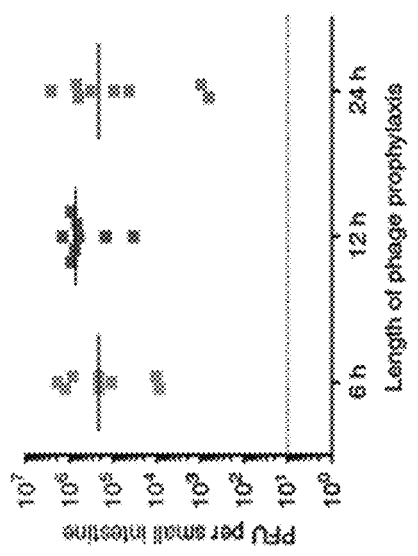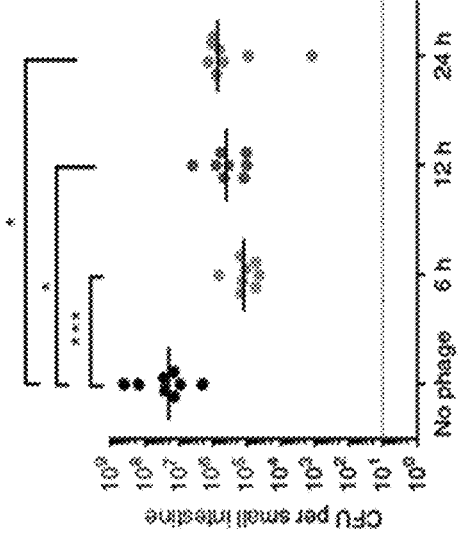
Fig. 3A  Fig. 3B  Fig. 3C  Fig. 3D  Fig. 3E

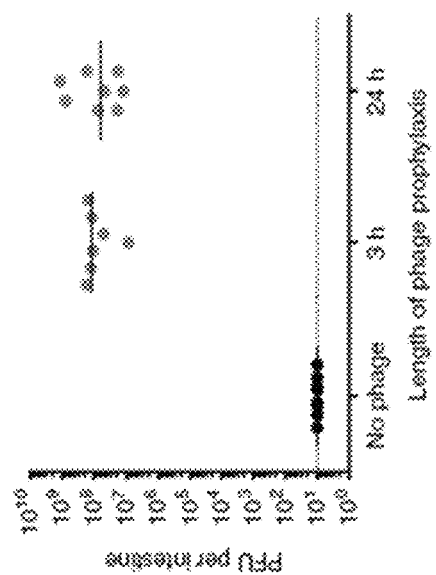
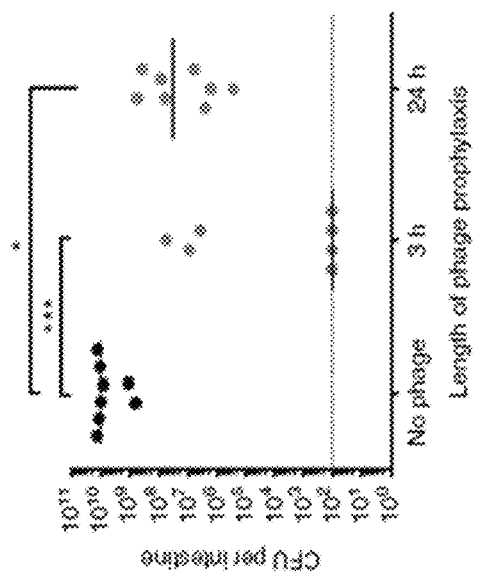
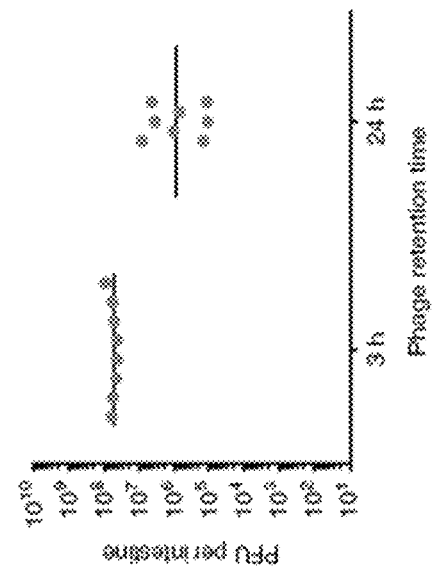
Fig. 4A
Fig. 4B
Fig. 4C

METHODS AND COMPOSITIONS FOR PREVENTING INFECTION BY A *VIBRIO* SPECIES

Related applications

The present application is a continuation of international application PCT /US2017/025305 entitled "Methods and compositions for preventing infection by a *Vibrio* species", filed Mar. 31, 2017, which is related to and claims the benefit of provisional application Ser. No. 62/316,704 entitled "Methods and compositions for preventing and treating an infection by a *Vibrio* species", filed Apr. 1, 2016 with inventors Andrew Carnilli, Minmin Yen and Lynne Cairns, each of which is hereby incorporated herein by reference in its entirety

GOVERNMENT SUPPORT

This invention was made with government support under grant A1055058 awarded by the National Institutes of Health. The government has certain rights in the invention.

BACKGROUND

Cholera is a diarrheal disease caused by multiplication and toxin production by *Vibrio cholerae* in the small intestine. Rapid transmission of cholera within households is a major source of new infections during outbreaks. The peak time of these secondary cases is 48 hours after the index case presents. Prophylactic antibiotic use is discouraged because of disruptions to the normal microbiota, and other agents are not readily available to treat or prevent this disease. The risk of infection increases approximately 100-fold in households of family members containing a patient with cholera, compared to those not having a patient.

Three strains of vegetative (lytic or virulent) *Vibrio* bacteriophages have been isolated and sequenced, ICP-1, ICP-2 and ICP-3. (Seed et al., *mBio*, 2(1):1-9, 2011). Each of these strains of phage has frequently been isolated from stool samples in cholera patients in Dhaka, Bangladesh. Rarely, two of these strains of phage were detected in a stool sample of a single cholera patient and PCR is needed as the incidence is rare, and all three strains of phage have not been detected together in the same sample.

Mutations of *Vibrio cholerae* in the genes encoding the ICP-1 receptor, which is the O1 antigen of the surface layer lipopolysaccharide (LPS), are selected, and mutants are resistant to phage infection (Seed et al., *PLoS Pathog*, 8(9):1-13, 2012). These mutations occur at a high frequency in vitro. During infection in animals or humans, the frequency decreases because *V. cholerae* lipopolysaccharide is required for bacterial virulence in the diseased intestinal tract.

A few strains of *V. cholerae* have a resistance mechanism against ICP-1 (Seed et al., *Nature*, 494 (7438): 489-491, 2013). However, ICP-1 phage strains have evolved a mechanism to overcome that resistance by a CRISPR/Cas system which allows the phage to maintain an infectious cycle.

The bacterial receptor for ICP-2 is a surface protein critical for virulence called OmpU (Seed et al., *eLife*, 3:e03497, 2014). Bacterial escape mutant strains were observed in a portion of patients and contain point mutations in the gene that encodes OmpU protein. Certain patients were observed to shed avirulent *V. cholerae* escape mutants that no longer express the OmpU protein, these mutants not transmitting disease to other people.

There is a need for non-antibiotic agents that prevent transmission of cholera and related *Vibrio* bacterial diseases.

BRIEF DESCRIPTION OF THE DRAWINGS

FIGS. 3A-3E are graphical representations of PFU and CFU assays from the infant mouse small intestine model, showing that the *V. cholerae* burden of number of bacterial cells was reduced when phage are administered up to 24 h prior to bacterial infection. Symbols figures: ICP-1 shown as circles; ICP-2 as squares, and ICP-3 as triangles.

FIG. 3A shows the phage titer retained after 3 h, 6 h, 12 h, or 24 h, absent bacterial infection for each of the three phage strains: phage survived during the 24 hour period displaying a final titer from 100 to between about $10^6$ and about $10^7$. Circles are ICP-1, squares are ICP-2, and triangles are ICP-3.

FIG. 3B shows numbers of bacteria per small intestine following phage prophylaxis with phage cocktail of the three strains for the time period indicated before receiving the challenge dose of bacteria. Mice were treated with the phage cocktail in an amount of about from about $2\times10^5$ to about $5\times10^5$ PFU, then were challenged by infection with *V. cholerae* cells in an amount between about $5\times10^5$ to about $9\times10^5$. Mice were sacrificed 24 h after infection and bacterial CFU measured in intestinal homogenates. The data show that bacterial cell counts were several orders of magnitude reduced compared to control subjects not administered phage, with prophylaxis being greatest administered at 6 h prior to infection. Phage prophylaxis reduced the load of *V. cholerae* in the small intestine of 5-day-old mice when given up to 24 h before bacterial challenge. The phage cocktail was most effective administered at 6 h or 12 h before challenge, and even after administering at 24 h before challenge, the intestinal bacterial load was observed to have been reduced to about 100-fold lower than in control subjects not administered phage. The dotted line is the limit of detection. Even after prophylaxis with phage administered at 24 h prior to infection, the observed bacterial cell count was reduced at least by two orders of magnitude compared to control animals not administered phage.

FIG. 3C shows the phage PFU per small intestine following phage prophylaxis at either 6 h, 12 h or 24 h before infection of the animals in FIG. 3B, with maximal phage production observed in the animals administered phage at 24 h prior to bacterial challenge.

FIG. 3D shows surviving CFU of bacteria following prophylaxis with the three phage strain cocktail and challenge with a high dose (1 to $1.3 \times 10^8$ of the *V. cholerae* cells). The data show that CFU was reduced by at least about one to two orders of magnitude, with maximal efficacy observed following prophylaxis with phage administered 6 h prior to bacterial challenge.

FIG. 3E shows persistence of the phage titer of PFU in the intestinal samples shown in FIG. 3D.

FIGS. 4A-4C are graphs representing data obtained from infant rabbit subjects dosed with the phage cocktail at time points 3 h or 24 h before *V. cholerae* infection.

FIG. 4A shows the phage retention in the small intestine absent bacterial infection at the time points after dosing with $3 \times 10^8$ PFU of the ICP phage cocktail and sacrificing 3 h or 24 h later. Substantial numbers of phage as PFU were found to be retained at each time point, with a reduction to about 10% of the initial input phage after 3 h, and to about 1% after 24 h.

FIG. 4B shows the number of cells of *V. cholerae* observed in the small intestine of rabbits dosed with between $4 \times 10^9$ to $8 \times 10^9$ PFU of the phage cocktail and then challenged with $5 \times 10^8$ CFU of *V. cholerae* after 3 h or 24 h. The data show that in subjects dosed 3 h prior to challenge, more than half of the subjects showed no bacterial CFU within the limits of detection, and the remaining subjects had two to three orders of magnitude reduction in numbers of bacteria. As a result of phage prophylaxis administered 24 h prior to challenge, the number of *V. cholerae* bacteria per intestine was reduced by two to three orders of magnitude.

FIG. 4C shows an analysis of numbers of phage PFU in the subjects of FIG. 4B, after the *V. cholerae* challenge. The data show that high numbers of phage were present in the small intestines of the subjects, as expected if reduction of bacteria seen in FIG. 4B was due to lytic growth of the phage in the subjects infected with bacteria. Similar PFU were observed isolated from subjects that had been dosed prophylactically either at 3 h or at 24 h prior to the bacterial challenge.

FIG. 9A shows CFU data as in FIG. 3A, obtained from mice that were orally dosed with between $6 \times 10^6$ and $4 \times 10^7$ total PFU of the cocktail having the indicated ratio, respectively, of ICP-1:ICP-2:ICP-3, and a control group that were not treated with phage. After 24 h, mice were orally challenged with between $3 \times 10^5$ and $5 \times 10^5$ CFU of *V. cholerae*. After 24 h following the infection, the mice were sacrificed and number of CFU of *V. cholerae* surviving in the small intestine enumerated. The dotted line represents the limit of detection, and the horizontal solid bar represents the median. Each circle represents one animal. Significance was calculated using the Kruskal-Wallis test with the Dunn's post-hoc multiple comparisons test. *P=0.01-0.05, **P=0.001-0.01. The data show that ratios of 1:1:1 and 1:1:10 provided the most significant protection to the subjects.

FIG. 9B shows CFU data as in FIG. 3D, in which the phage cocktail was administered 12 hours prior to a high-dose *V. cholerae* challenge. Phage prophylaxis reduced *V. cholerae* colonization by one to two orders of magnitude in the small intestine when compared to the no-phage control group, and this result was observed with groups treated with the cocktail prepared at the different ratios of strains. Mice were orally dosed with between $6 \times 10^5$ and $2 \times 10^6$ total PFU of the indicated cocktail ratio and a control group was not treated with phage. Twelve hours later, mice were orally challenged with between $2 \times 10^8$ and $3 \times 10^8$ CFU of *V. cholerae*. After 24 h of infection, the mice were sacrificed and *V. cholerae* surviving in the small intestine enumerated by calculating CFU per small intestine. The dotted line represents the limit of detection, and the horizontal solid bar represents the median. Each circle represents one animal. Significance was calculated using the Kruskal-Wallis test with the Dunn's post-hoc multiple comparisons test. *$P=0.01$-$0.05$, ***$P=0.0001$-$0.001$. The data show that a ratio of 1:1:1 provided the most significant protection to the subjects.

SUMMARY

Figure 1A:
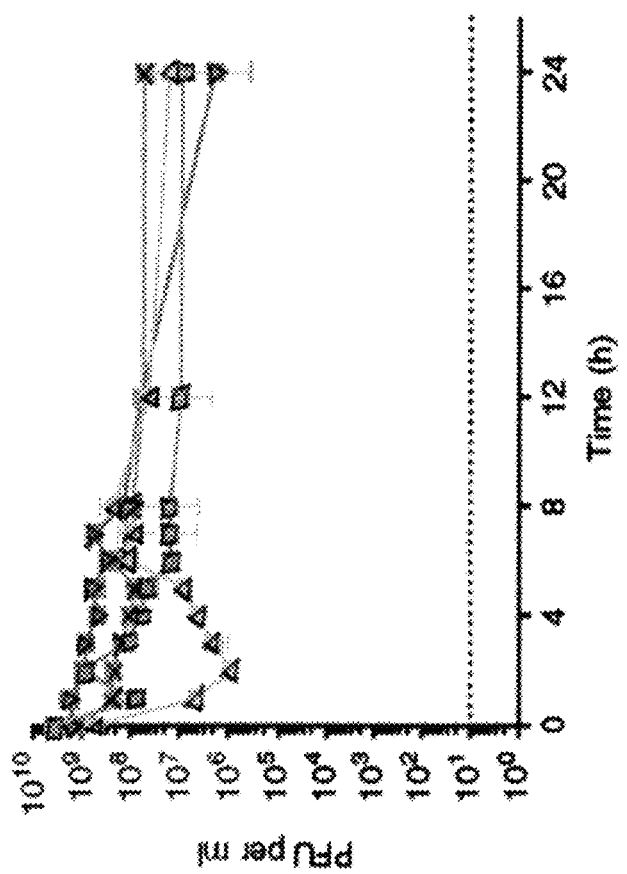
FIG. 1A is a set of growth curves of *V. cholerae* cultures in vitro in the presence of phage during a 24 h period, and a control culture lacking phage. Number of cells per ml is shown on the ordinate (log scale), as a function of time on the abscissa. The multiplicity of infection (MOI) of phage in each culture is 1 phage/cell. Black circles indicate growth of the control *V. cholerae* absent phage, the bacteria growing in an initial log phase achieving stationary phase within four hours. Growth of cells in presence of ICP-1 (triangles), ICP-2 (squares), ICP-3 (inverted triangles) or a phage cocktail mixture of these three strains (—x—) was retarded significantly, the cocktail reducing cell titer to an initial titer of $10^3$ per ml compared to $10^8$ cells per ml in the control without phage. Growth of bacteria in the presence of the cocktail of three phage strains was reduced at least three orders of magnitude during the initial 12 h, and remained reduced during the entire 24 h period.

An aspect of the invention herein provides a composition for preventing or reducing a *Vibrio* bacterial infection in a subject, the composition containing: a prophylactic mixture of a plurality of strains of lytic bacteriophage that infect and lyse cells of the bacterial infection *Vibrio* species. In an embodiment of the composition, the strains of lytic bacteriophage are isolates from stool samples of patients infected with *Vibrio cholerae*. For example, the plurality is at least two bacteriophage strains selected from the group consisting of: ICP-1, ICP-2, ICP-3, or virulent variants thereof. A particular embodiment of the composition is a cocktail in which the plurality includes bacteriophage strains ICP-1, ICP-2, and ICP-3. Additional embodiments include at least one of the strains being a variant or a mutant of a wild type bacteriophage, the variant selected from the group of spontaneous mutants, induced mutants, and genetically engineered recombinants. In general, the virions of the lytic strains of bacteriophage replicate in cells of the *Vibrio* infection species and lyse the cells, causing death of the bacteria in the subject, and so preventing or reducing the infection.

The terms, "virulent" and "lytic" as used herein refer to bacteriophage strains that infect bacteria and have a productive replicative cycle that results in death and lysis of the bacterial cell. The term, "lysogenic" or "temperate" refers to bacteriophage strains capable of lysogeny of the bacterial cell resulting in continued growth of the cell carrying the phage genome integrated into the bacterial chromosome. Lysogenic phage strains can mutate to virulent derivatives which are strictly lytic in growth and can be used in the compositions and methods herein.

The composition in any of the embodiments contains the plurality of strains in a ratio of the amount of plaque forming units (PFU) of each strain of any two of the plurality of the strains in the composition is in the range of from less than about 1:10 respectively, of the titers of a first and a second of the strains, respectively, to greater than 10:1 of the titers of the first and the second of the strains. The composition is suitable to administer to a subject who has not been previously been exposed to the *Vibrio* infection species, for example, to the best of the knowledge of the subject. Alternatively, the subject is exposed to the *Vibrio* infection species, for example, the exposed subject is a household member of a patient suffering from the infection, or the exposed subject is a medical worker.

To vastly reduce or even eliminate appearance of resistant mutants among the infected bacteria, the virions of the bacteriophage bind the surface of the *Vibrio* cell by attachment of the first strain to a first receptor on the bacterial surface, and attachment of the second strain to a second receptor, and the first and second receptors are molecularly different. In this way, the rate of spontaneous mutation to resistance, which is on the order of a frequency in a bacterial population of about $10^{-7}$ to about $10^{-9}$ for most bacterial genes, would need to be squared to obtain a double resistance mutant to two phage strains, which is a rate so low as to be negligible or even non-existent. Accordingly in embodiments of the composition herein, the virions of the first strain of bacteriophage bind to bacterial cell outer membrane protein OmpU and the virions of the second strain of bacteriophage bind to lipopolysaccharide.

A particular advantage of the compositions provided herein is that cells of strains of a normal microbiome lack receptors for the plurality of the bacteriophage strains, and the viabilities of the normal gut flora species remain unaffected. The host ranges of the strains of lytic bacteriophage comprise the *Vibrio* species of the infection. For example, the infection is cholera and the strains of lytic bacteriophage infect cells of *V. cholerae*. In some embodiments, the host ranges of the strains of lytic bacteriophage include ability to infect a plurality of *Vibrio* species. This genus of bacteria is responsible for diseases in a large number of animals species. For example, embodiments of the composition contain a plurality of bacteriophage strains with host ranges for the *Vibrio* species being at least one selected from the group consisting of: *Vibrio aerogenes, V. aestivus, V. aestuarianus, V. agarivorans, V. albensis, V. alfacsensis, V. alginolyticus, V. anguillarum, V. areninigrae, V. artabrorum, V. atlanticus, V. atypicus, V. azureus, V. brasiliensis, V. bubulus, V. calviensis, V. campbellii, V. casei, V. chagasii, V. cholerae, V. cincinnatiensis, V. coralliilyticus, V. crassostreae, V. cyclitrophicus, V. diabolicus, V. diazotrophicus, V. ezurae, V. fluvialis, V. fortis, V. furnissii, V. gallicus, V. gazogenes, V. gigantis, V. halioticoli, V. harveyi, V. hepatarius, V. hippocampi, V. hispanicus, V. ichthyoenteri, V. indicus, V. kanaloae, V. lentus, V. litoralis, V. logei, V. mediterranei, V. metschnikovii, V. mimicus, V. mytili, V. natriegens, V. navarrensis, V. neonates, V. neptunius, V. nereis, V. nigripulchritudo, V. ordalii, V. orientalis, V. pacinii, V. parahaemolyticus, V. pectenicida, V. penaeicida, V. pomeroyi, V. ponticus, V. proteolyticus, V. rotiferianus, V. ruber, V. rumoiensis, V. salmonicida, V. scophthalmi, V. splendidus, V. superstes, V. tapetis, V. tasmaniensis, V. tubiashii, V. vulnificus, V. wodanis*, and *V. xuii*.

In various embodiments, the composition further includes at least one therapeutic agent selected from the group of: an antibiotic, an antifungal, an anti-protozoan, an anti-inflammatory, an anti-dehydration, and a hydrating agent. The composition in alternative embodiments is formulated as one of the group selected from: a liquid, a tablet, a capsule, a food additive, and a lyophil. For a lyophil, the composition is packaged to include sterile buffer as a solvating agent.

An aspect of the invention herein provides a method of preventing or ameliorating a *Vibrio* species infection in a subject, the method including administering to the subject a composition comprising a prophylactic dose of a plurality of lytic bacteriophage strains that infect and lyse cells of the *Vibrio* infection species. For example, the *Vibrio* species is at least one selected from the group consisting of: *Vibrio aerogenes, V. aestivus, V. aestuarianus, V. agarivorans, V. albensis, V. alfacsensis, V. alginolyticus, V. anguillarum, V. areninigrae, V. artabrorum, V. atlanticus, V. atypicus, V. azureus, V. brasiliensis, V. bubulus, V. calviensis, V. campbellii, V. casei, V. chagasii, V. cholerae, V. cincinnatiensis, V. coralliilyticus, V. crassostreae, V. cyclitrophicus, V. diabolicus, V. diazotrophicus, V. ezurae, V. fluvialis, V. fortis, V. furnissii, V. gallicus, V. gazogenes, V. gigantis, V. halioticoli, V. harveyi, V. hepatarius, V. hippocampi, V. hispanicus, V. ichthyoenteri, V. indicus, V. kanaloae, V. lentus, V. litoralis, V. logei, V. mediterranei, V. metschnikovii, V. mimicus, V. mytili, V. natriegens, V. navarrensis, V. neonates, V. neptunius, V. nereis, V. nigripulchritudo, V. ordalii, V. orientalis, V. pacinii, V. parahaemolyticus, V. pectenicida, V. penaeicida, V. pomeroyi, V. ponticus, V. proteolyticus, V. rotiferi-*

*anus, V. rubes, V. rumoiensis, V. salmonicida, V. scophthalmi, V. splendidus, V. superstes, V. tapetis, V. tasmaniensis, V. tubiashii, V. vulnificus, V. wodanis*, and *V. xuii*.

In various embodiments, the subject is selected from a human, a farm animal, a zoo animal such as a koala, a high value mammal such as a dog or a horse, a laboratory animal such as a rodent or a rabbit, a fish, and a bird such as a parrot or a parakeet. For example, the subject is a human selected from a household member or a family member of a patient, and a medical worker such as a doctor, a nurse, or an orderly. In an embodiment of the method, the administering step is oral.

An embodiment of the method further includes, after the administering step, analyzing amount of reduction of the *Vibrio* cell load in the gastrointestinal tract whereby administering results in reducing the load of the *Vibrio* species cells in the subject and preventing colonizing of the subject by the *Vibrio* bacteria. The analyzing step includes the non-invasive method of assaying stool samples by DNA content or by selective solid medium use for counting bacterial colonies. The bacteriophage present in the treated subject can be analyzed as PFU excreted in stool samples or by other methods. The method in various embodiments further includes administering at least one of a rehydration therapy agent and at least one antibiotic. The method further includes, following the administering step, analyzing content of bacterial flora of the microbiota of the host. In an embodiment of the method, the administering step is after exposure to the *Vibrio* infection species, and the method comprises ameliorating the infection. In alternative embodiments the administering is after the exposure and prior to onset of symptoms of cholera, or, the administering is prior to the exposure and the method is preventing or ameliorating infection, or some combination is used.

The method in various embodiments, further includes, prior to the administering step, formulating the composition to a bacteriophage total titer of at least about $10^7$, about $10^8$, about $10^9$, about $10^{10}$, about $10^{11}$, about $10^{12}$, or at least about $10^{13}$ PFU/ml. Formulating the composition of titers in PFUs of at least two of the plurality of strains further includes making the composition by mixing the strains in a ratio range of from less than about 1:10, to at least about 1:5, to at least about 1:1, to at least about 5:1, to at least about 10:1, respectively of the titer of a first strain to that of a second strain. Prior to formulating the composition by mixing the phage strains, the method includes prior to the administering step, culturing each of the lytic bacteriophage strains with an avirulent *Vibrio* species host.

An embodiment of the method further includes, prior to the administering step, formulating the composition for limiting selection of escape phage resistant mutants in the subject. For example, the method further includes, prior to the administering step, formulating the composition by selecting at least two strains from the group consisting of: ICP-1, ICP-2, ICP-3, strain 138, strain 145, strain 163, and lytic variants thereof. For example, the composition is administered in a dose of at least about $10^7$, about $10^8$, about $10^9$, about $10^{10}$, about $10^{11}$, about $10^{12}$, or at least about $10^{13}$ PFU/dose, which amount that is selected depends upon the size, age, and stage of illness of the subject to be treated.

The method includes, in one embodiment, re-iterating the administering step. The method includes, in one embodiment, administering an antibiotic. The method includes, in one embodiment prior to administering, isolating the strains of lytic bacteriophage from an environmental sample or from a *Vibrio* infected subject. For example, the subject is a human and the sample is a stool sample of the infected subject. The method includes, in one embodiment prior to administering, formulating the composition by encapsulating the virion mixture of the bacteriophage strains.

An aspect of the invention herein provides a kit comprising a unit dose of the composition formulated for treatment of a human, containing an amount of the phage cocktail including a plurality of strains of lytic bacteriophage, each of the strains capable of infecting and lysing cells of a species of *Vibrio* bacteria.

DETAILED DESCRIPTION

An embodiment of the composition herein is a cocktail suspension of three naturally occurring virulent bacteriophage strains for use in preventing cholera in people at high risk. This composition is administered by oral ingestion and protects from *V. cholerae* colonization and disease in animal models when administered at $10^8$ PFU up to 24 hours before challenge. The bacteriophage strains are grown on an avirulent *V. cholerae* host, purified to near homogeneity by polyethylene glycol precipitation, and resuspended in saline to a final titer of $10^9$ PFU/ml.

The intervention of prophylactic antibiotic use is discouraged because of disruptions to the normal microbiota. "Phage prophylaxis", viz., administration of a phage cocktail to prevent development of a *Vibrio*-associated disease, can be used instead by orally administering a composition which is a cocktail of two or more strains of virulent, *V. cholerae*-specific bacteriophage strains, as demonstrated herein. Use of different bacteriophage strains, each of which targets a different cell receptor and the importance of these receptors as virulence factors of *V. cholerae*, greatly limits the appearance of bacterial escape mutants within patients.

The three naturally occurring bacteriophage strains which were used prophylactically to prevent cholera in animal models of infection are envisioned to work similarly in humans to prevent cholera. The target population to receive phage prophylaxis includes household contacts of cholera patients, others at high risk of exposure such as medical personnel, and people in the general population recently exposed but still asymptomatic. Examples herein show that administering the phage cocktail orally to each of mice or rabbits protects them for up to 24 hours (the longest time tested thus far) from subsequent challenge with a lethal dose of *Vibrio cholerae*. It was further observed that the load of *V. cholerae* in the small intestine, which is the site of infection in animals and humans, is greatly reduced, and that the animals exhibit no signs of diarrhea or weight loss.

Each strain of phage in the cocktail of embodiments of the compositions provided herein is of the virulent phage type, meaning it continually engages in rounds of infection and lysis of *V. cholerae* cells, as opposed to temperate or lysogenic phage strains, which usually both lyse (kill) and lysogenize host bacterial cells. Each of the three strains of phage specifically infects and kills *V. cholerae*, and not other species of bacteria i.e., each strain has a very narrow one species host range, or a one genus host range, although not all species of *Vibrio* have been tested. Thus an advantage of the phage cocktail herein compared to antibiotics or broad host-range phages would be no disruption of the normal flora species of host microbiota in the subject, leading to fewer side effects such as gastrointestinal distress. Another advantage compared to antibiotics is that the phage virions replicate in the presence of *V. cholerae*, and thus can quickly increase in number to keep *V. cholerae* in check. Although the three phage strains in the composition are found naturally in the secretory diarrhea of some cholera patients, it has never been observed that all three phage strains appear together in nature, and thus the present composition of our cocktail is novel.

Reduction in bacterial colonization by administering bacteriophage compositions is shown by Morris et al., U.S. Pat. No. 8,003,323 issued Aug. 23, 2011, for *Staphylococcus aureus* and for vancomycin-resistant *Enterococcus*, Gram-positive bacterial species that are the most common causative agents of nosocomial (hospital acquired) bacteremias. Gram-positive bacterial strains differ substantially from Gram-negative bacteria, for example, as the latter contain an outer membrane composed of lipopolysaccharide. This major difference accounts not only for ability to stain using classical techniques, but for various medical properties including antibiotic sensitivity, interaction with the human immune system, and for a spectrum of microbiological and environmental properties.

Compositions and methods are provided herein for prevention and treatment of infections of humans and various animal species by the Gram-negative bacterial pathogens of the genus *Vibrio*. Detailed methods of growth conditions for *Vibrio* bacterial cultures and infection with phage, and preparation and purification and titration of phage are shown in Seed et al., *mBio,* 2(1): 1-9 (2011) which is hereby incorporated herein by reference in its entirety. Methods for bacterial strain construction and for manipulating and obtaining recombinant bacterial strains are shown in Seed et al., *PLoS Pathog,* 8 (9): 1-13 (2012) which is hereby incorporated herein by reference in its entirety. Methods for isolation of phage from natural environmental samples and from stool samples, and characterization of these strains are shown in Seed et al., *eLife,* 3:e03497 (2014) which is hereby incorporated herein by reference in its entirety. Methods for use of phage as anti-bacterial agents are shown in Ly-Chatain, M., *Frontiers in Micro.* 5: article 51: 1-7 (2014), and methods for micro-encapsulation of phage strain Felix for treatment of *Salmonella* infection are shown in Ma, Y. et al., *App.Environ.Micro.* 74 (15): 4799-4805 (2008). Methods for isolation and characterization of phage strain CP-T1, a generalized transducing strain of *Vibrio* phage and mutagenesis to obtain temperature-sensitive plaques are shown in Hava, D. et al., *J. Micr. Methods,* 46: 217-225 (2001). These methods are envisioned as readily adaptable for isolation of a virulent clear plaque-forming variant of this phage strain for use in a composition of the present claims. Modification of bacteriophage to delay inactivation by the host defense system, such as serial cultivation in vivo in mice of UV-mutagenized phage lambda or insertion mutagenesis of the OrfX gene of this phage strain for *Escherichia coil*, are described by Merril et al., U.S. Pat. No. 5,766,892 issued Jun. 16, 1998.

The word "phage" as used herein is a shortened form of the term, "bacteriophage", which are bacterial-specific viruses, and these words as used herein are interchangeable. The phrase "rice-water stool" as used herein shall mean secretory diarrhea shed by cholera patients. The phrase, "cecal fluid" as used herein with respect to *V. cholerae* means fluid in the cecum of infected, symptomatic (cholera symptoms) subjects or patients. For example, infant rabbits provide an animal model and produce cecal fluid, which is highly similar to human rice-water stool, hence these animals are used as an animal model system for cholera.

The abbreviation, "$ID_{50}$" as used herein means the amount of bacteria that results in infection of half of the animals. The abbreviation "CFU" means colony-forming units, which is a measure of the number of live bacterial cells. The cecal fluid of infected animals contains about $10^8$ CFU/ml of *V. cholerae*. The phrase, "multiplicity of infection" (MOI) means the ratio of number of phage added to a number of bacteria. For example, an MOI of 0.1 means one phage virion for every ten bacterial cells, and an MOI of 5 means 5 phage for every bacterial cell.

The phrase, "phase variation" as used herein refers to a high frequency, reversible genetic change that results in change in phenotype, commonly used to refer herein to a mutation in bacterial cells to resistance to phage. The phrase, "null mutation" refers to a mutation that knocks out function of the protein encoded by the gene carrying the mutation.

The abbreviation, "PFU", means plaque-forming units, which is a measure of the number of infectious phage particles (virions) or phage titer. The phrase "virulent phage" refers to a type of phage that multiplies purely in a lytic manner, and produces clear plaques. Virulent phage strains contrast with "lysogenic" strains of phage, which have an alternative life cycle in which they can integrate DNA into a bacterial cell, and in so doing become a portion of the bacterial genome, then remain dormant although a portion will grow lytically thereby producing turbid plaques. The term, "lytic" shall have the same meaning as "virulent" with respect to characteristic of the life cycle of a strain of bacteriophage.

The abbreviation, "LPS" stands for lipopolysaccharide, which forms the surface monolayer of the outer membrane lipid bilayer, and these terms are used interchangeably. The outer membrane is the outermost surface of Gram-negative bacteria such as *Vibrio cholerae*. The word, "O-antigen" refers to the repeating oligosaccharide portion of LPS, which extends out from the surface of the bacterial cell. It is often targeted by the human immune system, thus explaining its name. The O-antigen is the receptor for many, but not all strains of phage. For *V. cholerae* serogroup O1, which is the cause of the vast majority of cases of cholera in the world, the O-antigen is comprised of 12-18 repeats of the tetronate-linked perosamine. About 200 O-antigen type or serogroups have been characterized within the *V. cholerae* species, and these are designated O1 through O200.

The life cycle of pathogenic *V. cholerae* is reviewed in Nelson, et al. *Nat Rev Microbiol.* October; 7(10):693-702, 2009. About half of cholera patient rice-water stool samples contain high titers of virulent (lytic) phage (Nelson et al. *Proc. Natl Acad. Sci. USA* 104, 19091-19096, 2007, PMCID: PMC2141913), an observation first reported 86 years ago (d'Herelle et al. *Ind. Med. Gaz.* 62:614-616, 1927). Scientists have surmised (d'Herelle et al. *Ind. Med. Gaz.* 62:614-616; 1927; Pasricha et al. *Ind. Med. Gaz.* 66, 543-550, 1931; Faruque et al. *Proc. Natl Acad. Sci. USA* 102, 1702-1707, 2005; Jensen et al. *Proc. Natl Acad. Sci. USA* 103, 4652-4657, 2006; Faruque et al. *Proc. Natl Acad. Sci. USA* 102, 6119-6124, 2005) that lytic phage may impact transmission and dissemination of *V. cholerae*. However, only circumstantial evidence regarding potential impact has been reported (d'Herelle et al. *Ind. Med. Gaz.* 62:614-616, 1927; Faruque et al. *Proc. Natl Acad. Sci. USA* 102, 1702-1707, 2005; Faruque et al. Proc. Natl Acad. Sci. USA 102, 6119-6124, 2005).

Accordingly, examples herein analyze extent of impact of a cocktail of two or more lytic phage strains, on infectivity of *V. cholerae*. Examples herein show that lytic phage reduce the load of *V. cholerae* in the small intestine in a dose-dependent manner (Nelson et al. *PLoS ICP*-2. 4, e1000187, 2008, PMCID: PMC2563029). Examples herein represent the first controlled laboratory demonstrations of phage therapy against *V. cholerae*.

The therapeutic potential of lytic phage was investigated in examples herein in a retrospective study performed using archived rice-water stools obtained in Bangladesh. It was discovered that, although some lytic phage were transient over the ten-year period examined, one phage that is designated ICP-1 was found to have remained omnipresent during this period (Seed et al. *mBio.* 2(1). pii: e00334-10 (2011). PMCID: PMC3037004), and remains present today. It is here envisioned that ICP-1 may have adapted to associate closely with epidemic *V. cholerae* strains. In studying the interactions of ICP-1 with *V. cholerae*, it was discovered that *V. cholerae* uses phase variation for rapid generation of ICP-1-resistant mutants in vitro and in a pond microcosm (Seed et al. *PLoS ICP*-2. 8(9):e1002917 (2012). PMCID: PMC3441752). The phase variants have a truncated LPS O-antigen, and wild type LPS was determined to be the receptor for ICP-1. Further, the bacterial phase variants were found to be attenuated for ability to cause infection, explaining why such mutants were not found in patient stool samples. Thus ICP-1 is able to enter humans in association with cells of *V. cholerae* where the phage continue to propagate.

Some strains of *V. cholerae* use another defense mechanism, which is a phage-inducible chromosomal island-like element (PLE) that specifically interferes with ICP-1 replication (Seed et al. *Nature.* 494(7438):489-91 (2013). PMCID: PMC3587790). Surprisingly, it was discovered that half of ICP-1 isolates possess a functional CRISPR/Cas system dedicated to circumventing the PLE by targeting it for destruction (Seed et al. *Nature.* 494(7438):489-91, 2013). This is the first report of a PLE in Gram-negative bacteria, and also the first report of a functional CRISPR/Cas encoded by a phage. Several classical biotype strains were found, including one isolated in Iraq in 1931, that contain PLEs dedicated to defense against ICP-1. Thus the molecular battle between bacteria and phage has been ongoing for at least 80 years.

Another lytic phage strain, ICP-2, originally isolated in Bangladesh, exerts selective pressure on *V. cholerae* during human infection in Bangladesh and Haiti in a way that dramatically alters the population structure of the shed bacteria. ICP-2 is the only lytic phage identified so far in samples obtained from the Haiti epidemic. Some patients shed ICP-2 resistant mutants which were characterized as harboring single amino acid changes in one of two extracellular loops of the major outer membrane protein OmpU, which is the receptor for ICP-2. OmpU is known to be a critical virulence factor of *V. cholerae* and its expression is highly upregulated during infection of the intestinal tract. The single amino acid mutants retain OmpU expression and at least partial function, since several mutants tested remained virulent. However, they suffer a modest fitness defect during growth outside the host. This fitness defect may explain why mutant OinpU alleles have not become fixed in the population. Interestingly, other patients were observed to shed a different type of ICP-2-resistant mutant bacterial strain, having null mutations in ToxR. ToxR is a positive transcriptional regulator of ompU and virulence genes. Thus, the shed population from these patients is ICP-2-resistant. The cells of these bacteria fail to express the normal amount of OmpU in the outer membrane. These bacteria lack virulence gene expression. It was envisioned that these different populations were selected according to the stage during the human infection of the phage bloom, which would have exerted selective pressure on *V. cholerae*. For example, null mutations in ToxR presumably would not be tolerated early in the infection, but would be inconsequential late in the infection when the bacterial burden is high and cholera toxin has already elicited secretory diarrhea.

Multi-faceted approaches are required to combat infectious diseases, particularly in an era in which antibiotics are losing effectiveness as multiple drug resistance in bacteria becomes worldwide. Effective prevention strategies will be essential in reducing disease burden due to bacterial infections. Accordingly, embodiments of the compositions and methods provided herein harness the specificity and rapid-acting properties of bacteriophages as a prophylaxis therapy for diseases caused by the bacterial genus *Vibrio*, particularly cholera, a severely dehydrating disease caused by the etiological agent *Vibrio cholerae*. Using a composition that is a mixture or a cocktail of three virulent phages, methods herein with two animal models of cholera pathogenesis indicate that this approach was successfully used to reduce disease. Oral administration of the phages up to 24 hours before *V. cholerae* challenge reduced colonization of the intestinal tract and prevented cholera-like diarrhea. Surviving *V. cholerae* colonies were tested for phage sensitivity, and none were resistant to all three phages. Genome sequencing and variant analysis indicated that resistance was largely conferred by mutations in genes required for the production of the phage receptors. Further, it is likely that the resistant strains observed are impaired for virulence. For acute infections such as cholera and related diseases caused by *Vibrio* species, phage prophylaxis offers a potential strategy to limit the impact of bacterial disease on human health.

Cholera is an acute, severely dehydrating diarrheal disease caused by the water-borne bacterium *Vibrio cholerae*. Cholera remains a substantial global health burden and is endemic to many parts of Africa and Asia (Zuckerman et al. *The Lancet Infectious Diseases* 7, 521-530, 2007). Recent widespread epidemics in disaster-stricken or war-torn countries such as Haiti (Luquero et al. *Emerging infectious diseases* 22, 410-416, 2016) and Iraq (Bagcchi, S. *The Lancet Infectious Diseases* 16, 24-25, 2016) highlight the vulnerabilities of populations to sudden outbreaks. Current recommended preventatives include mass vaccinations with the WHO-prequalified oral cholera vaccine (Qadri et al. *The New England J Med* 374, 1723-1732, 2016) and increased awareness of sanitation and hygiene practices (Taylor et al. *PloS One* 10, e0135676, 2015). Access to clean water, however, is difficult, and vaccination campaigns require forethought and time for efficacy; both methods are not logistically feasible for immediate protection in the event of an outbreak.

Household transmission is a major contributor to the rapid spread of *V. cholerae* within communities. Household contacts of index cases often present with cholera symptoms two to three days after the initial patient becomes sick (Harris et al. *PLoS neglected tropical diseases* 2, e221, 2008). Therefore, there is currently an unmet need for a clinical intervention to stem the household spread of cholera by use of a rapid prophylactic treatment. While chemoprophylaxis with antibiotics may effectively reduce cholera burden (Reveiz et al. *PloS one* 6, e27060 (2011), the WHO does not recommend this practice due to the development and spread of drug-resistant bacteria (WHO, 2014). Moreover, the broad-spectrum action of antibiotics would cause dysbiosis of the resident intestinal microbiota, which could put patients at risk of other intestinal infections.

Interest in the use of bacteriophages (phages) for environmental and clinical applications has been manifest since the discovery of bacteriophage almost a century ago (Wittebole et al. *Virulence* 5, 226-235, 2014). In contrast to antibiotics, phage strains are specific in bacterial targets and, because they are replicating viruses, are capable of auto-dosing, a phenomenon by which phage replication increases the total titer or number of live phage capable of forming plaques (plaque forming units, PFU), and contributes to the dose.

Previous attempts to use phages to prevent or treat cholera have produced mixed results. Dutta et al. *Bull. Wld Hlth Org.* 28, 357-360 (1963) showed that a single phage type given one hour before *V. cholerae* challenge in an infant rabbit model prevented onset of cholera symptoms. Jaiswal et al. *Microbes and Infection* 15, 152-156 (2013) showed that a cocktail of five lytic bacteriophage types given 6 or 12 hours prior to *V. cholerae* challenge in an adult rabbit model reduced diarrheal severity slightly but failed to significantly lower the bacterial load. A second study in adult mice did not address prophylaxis as phage were not administered prior to challenge with the pathogenic bacteria (Jaiswal et al. International *Journal of Medical Microbiology* 304, 422-430, 2014).

Three isolated *V. cholerae*-specific, lytic (virulent) phages ICP-1, ICP-2, and ICP-3, were isolated from rice-water stool samples of cholera patients in Bangladesh (Seed et al. *mBio* 2, e00334-00310, 2011). The receptors for ICP-1 and ICP-2, respectively, were identified as the lipopolysaccharide (LPS) O1 antigen (Seed et al. *PLoS Pathog* 8, e1002917, 2012) and the major outer membrane porin OmpU (Seed et al. *eLife* 3, e03497, 2014), respectively, which are considered virulence factors of *V. cholerae*. The receptor for ICP-3 is as yet unknown, although at least a partial role is visualized for the LPS O-antigen. These virulent phages were shown to impose significant bactericidal pressure on *V. cholerae* during its natural course of infection in humans (Seed et al. *eLife* 3, e03497, 2014).

A cocktail that contains different strains of phage that target different receptors would reduce the likelihood of multi-phage-resistant *V. cholerae* isolates in the surviving population. The receptors are different from each other because they have different chemical compositions, or are encoded by genes that are different, or arise from different molecular pathways. Therefore, it is visualized herein that a cocktail of the three ICP phages is a potential prophylaxis treatment to specifically target *V. cholerae* that transits into the small intestine to prevent signs of cholera in animal models of disease.

Examples herein show that orally applied, prophylactic use of the ICP cocktail prevented colonization by *V. cholerae* in the infant mouse model. The ICP cocktail also prevented the onset of cholera symptoms in the infant rabbit model when administered up to 24 hours prior to *V. cholerae* challenge. This proof-of-principle study demonstrates the successful use of phage prophylaxis to prevent disease caused by a mucosal pathogen.

A portion of this work has been published in a scientific paper entitled, "A cocktail of three virulent bacteriophages prevents *Vibrio cholerae* infection in animal models", co-authored by the inventors herein Yen, M, Cairns, L. S. and A. Camilli, Nat. Commun. 8:14187, Feb. 1, 2017 and which is hereby incorporated herein by reference in its entirety.

Pharmaceutical Compositions

In one aspect of the present invention, pharmaceutical compositions are provided, that comprise a plurality of virions (a virus capable of causing a plaque forming unit, PFU) of at least two *Vibrio* bacteriophage strains that have lytic (vegetative or virulent) replication cycles. The compositions optionally further comprise a pharmaceutically acceptable carrier. In certain embodiments the composition is encapsulated or micro-encapsulated. In certain embodiments, these compositions optionally further comprise one or more additional therapeutic agents. In certain embodiments, the additional therapeutic agent or agents are selected from the group consisting of growth factors, anti-inflammatory agents, vasopressor agents, collagenase inhibitors, topical steroids, matrix metalloproteinase inhibitors, ascorbates, angiotensin II, angiotensin III, calreticul in, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), and hyaluronic acid.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences* Ed. by Gennaro, Mack Publishing, Easton, Pa., 1995 discloses various carriers used in formulating pharmaceutical compositions and known techniques for the preparation thereof. Some examples of materials which can serve as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and anti-oxidants can also be present in the composition, according to the judgment of the formulator.

Therapeutically Effective Dose

In yet another aspect, according to the methods of treatment of the present invention, the prevention of transmission of the pathogenic *Vibrio* is promoted by contacting family members or other subjects at risk for the disease, and administering the pharmaceutical composition, as described herein. Thus, the invention provides methods for the treatment of a bacterial disease associated with a particular species of *Vibrio* comprising administering a therapeutically effective amount of a pharmaceutical composition comprising active agents that include at least two strains of the vegetative *Vibrio* bacteriophages, in such amounts and for such time as is necessary to achieve the desired result. It will be appreciated that this encompasses administering an inventive pharmaceutical as a therapeutic measure to prevent onset of the bacterial infection or prevent further development of the infection, or as a prophylactic measure to minimize complications associated with development of the bacterial infection.

In certain embodiments of the present invention a "therapeutically effective amount" of the pharmaceutical composition is that amount effective for preventing further development of a bacterial infection. The compositions, according to the method of the present invention, may be administered using any amount and any route of administration effective for prevention of development of infection. Thus, the expression "amount effective for prevention of infection", as used herein, refers to a sufficient amount of composition to prevent or retard development of the target *Vibrio* species, and even cause regression of or recovery from an onset of the previously acquired infection. The exact dosage is chosen by the individual physician in view of the patient to be treated. Dosage and administration are adjusted to provide sufficient levels of the active agent(s) or to maintain the desired effect. Additional factors which may be taken into account include the severity of the disease state, e.g., symptoms of infection; age, weight and gender of the patient; diet, time and frequency of administration; drug combinations; reaction sensitivities; and tolerance/response to therapy. Long acting pharmaceutical compositions might be administered once daily, or every 3 to 4 days, every week, or once every two weeks depending on half-life and clearance rate of the particular composition. It is within the bounds of the particular invention that successful treatment may require only a single dose, as the bacteriophage strains of the composition are bacterial viruses which are self-replicating within the disease-causing unwanted *Vibrio* cells.

In general an appropriate dosage for a small animal subject which has a weight of about 10 g to about 200 g, a suitable dosage is in the range of about $10^4$ to about $10^8$ PFUs total of the cocktail or mixture composition of the plurality of bacteriophage strains, depending on the size of the subject. For example, a suitable range of PFUs total of the cocktail or mixture composition of the plurality of bacteriophage strains, for a small animal such as an infant mouse or an infant rabbit, is from about $10^4$ to about $10^5$, or from about $10^5$ to about $10^6$, or from about $10^6$ to about $10^7$, or from about $10^7$ to about $10^8$, or from about $10^8$ to about $10^9$. For a human patient or a large animal subject, a suitable range is from about $10^7$ about $10^{11}$. For example, a suitable dose for a subject weighing from about 20 kg to about 200 kg, of PFUs total of the cocktail or mixture composition of the plurality of bacteriophage strains might contain from about $10^7$ about $10^8$, or might contain from about $10^8$ about $10^9$, or might contain from about $10^9$ about $10^{10}$, or might contain from about $10^{10}$ to about $10^{11}$ depending on the size, age and health of the patient or subject. A skilled veterinarian treating a very high value farm or zoo animal, for example, a stallion race horse or an endangered white rhinoceros would be able to scale up the suitable dosage and range from a dosage for a 200 kg patient to a animal weighing 850 kg, 1000 kg, 1600 kg or more.

The active agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total single or more frequent such as daily usage of the compositions of the present invention will be decided by the attending physician within the scope of sound medical judgment. For any active agent, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. A therapeutically effective dose refers to that amount of active agent which ameliorates the symptoms or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies are used in formulating a range of dosage for human use.

The effective dose is expressed as plaque forming units (PFU) as measured in *Vibrio* cells in a laboratory, based on known titers of stock solutions prepared according to the methods described herein and in attached Appendix A and in the references cited herein and hereby incorporated by reference herein. A stock solution contains at least about, for example, $10^{10}$, $10^{11}$, or about $10^{12}$ PFU/ml. A dose suitable for a small subject such as an infant might contain about $10^9$ or $10^{10}$ PFU, and a dose for a 100 kg subject might be an order of magnitude greater. It is within the knowledge of an attending physician to determine tolerance and requirement, based on prior exposure of the subject to persons infected by the *Vibrio* disease.

Administration of Pharmaceutical Compositions

After formulation with an appropriate pharmaceutically acceptable carrier in a desired dosage, the pharmaceutical compositions of this invention can be administered to humans and other mammals topically (as by powders, ointments, or drops), orally, rectally, parenterally, intracisternally, intravaginally, intraperitoneally, bucally, ocularly, or nasally, depending on the severity and location of the exposure to patients having active infections, and to the strain of the *Vibrio* being treated.

Liquid dosage forms for oral administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular or cutaneous infections may be treated with aqueous drops, a mist, an emulsion, or a cream. Administration may be therapeutic or it may be prophylactic. Prophylactic formulations may be present or applied to the site of potential infection, or to sources of the infection, such as contaminated water, food, fecal exposure, or cuts and wounds. The ointments, pastes, creams, and gels may contain, in addition to an active agent of this invention, excipients such as animal and vegetable fats, oils, waxes, paraffins, starch, tragacanth, cellulose derivatives, polyethylene glycols, silicones, bentonites, silicic acid, talc, zinc oxide, or mixtures thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms or forms for oral administration are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable and oral formulations are also prepared by entrapping the agent in liposomes or microemulsions which are compatible with body tissues.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

Uses of Pharmaceutical Compositions

As discussed above and described in greater detail in the Examples a pharmaceutical composition containing at least two different strains of lytic bacteriophage that infect and replicate within bacterial cells *Vibrio* is useful to prevent development or progression of the bacterial infection. In general, it is believed that these compositions will be clinically useful in preventing further infection and epidemic and pandemic development of the infection in humans, such as cholera caused by *Vibrio cholerae*, or in an animal having a corresponding disease caused by the same or by a different species of *Vibrio*.

It will be appreciated that the diagnostic, prognostic and therapeutic methods encompassed by the present invention are not limited to treating conditions in humans, but may be used to treat similar conditions in any mammal including but not limited to bovine, canine, feline, caprine, ovine, porcine, murine, and equine species. When treating an infection in a given animal species, the suitable lytic bacteriophage that infects and kills the cells of the *Vibrio* infectious to the species, are readily available in the environment in which animal is found. Accordingly the methods herein are envisioned as applicable to these conditions also.

EXAMPLES

Example 1. Growth Conditions and Strains

Bacteriophage strains and bacterial strains used in this study are listed in Tables 1 and 2. *V. cholerae* strains were grown in Luria-Bertani (LB) broth supplemented with 100 µg/ml streptomycin (Sm). The ICP cocktail comprises the *Vibrio* phages ICP-1, ICP-2, and ICP-3 in equal number. These phages were previously isolated from Bangladeshi cholera patient rice-water stool samples. ICP-1 was isolated on strain AC4741 while ICP-2 and ICP-3 were isolated on AC53, an Sm-resistant isolate of E7946. All examples were carried out using AC53 *V. cholerae* O1 El Tor strain E7946. Strains AC4653 and AC2846 were used in plaque assays as negative controls. ICP-1 and ICP-3 cannot form plaques on bacterial strain AC4653, and ICP-2 cannot form plaques on bacterial strain AC2846.

TABLE 1

Isolation of ICP-1, ICP-2 and ICP-3 from cholera patient stools, and phage characteristics

| Year | ICP-1 | ICP-2 | ICP-3 |
|---|---|---|---|
| 2001 | ∘ + ∘ | | |
| 2002 | ∘ ∘ ∘ | ∘ | |
| 2003 | ∘ ∘ + | | |
| 2004 | + ∘ ∘ | + | |
| 2005 | ∘ ∘ + | ∘ | |
| 2006 | ∘ + | + ∘ | |
| 2007 | ∘ ∘ ∘ | ∘ | + + |
| 2008 | ∘ ∘ ∘ | | + ∘ |
| 2009 | ∘ ∘ ∘ | | + ∘ |
| 2010 | ∘ ∘ ∘ | | ∘ |

TABLE 1-continued

Isolation of ICP-1, ICP-2 and ICP-3 from cholera patient stools, and phage characteristics

|  | ICP-1 | ICP-2 | ICP-3 |
|---|---|---|---|
| Feature: | | | |
| Taxonomic family | Myoviridae | Podoviridae | Podoviridae |
| Genome size, bp | 125,956 | 49,675 | 39,162 |
| Predicted proteins | 230 | 73 | 54 |
| % hypothetical | 88 | 81 | 52 |
| Receptor | O1-antigen | OmpU | O1-antigen |

Symbols:
+ indicates plaque-positive;
o indicates PCR-positive

TABLE 2

Bacterial strains

| Strain | Description |
|---|---|
| AC53 | *V. cholerae* O1 El Tor Ogawa E7946 (Sm$^R$) |
| AC2846 | E7946 ΔompU |
| AC4653 | E7946 ΔwbeL |
| AC4741 | *V. cholerae* O1 El Tor Ogawa (Sm$^R$), PLE negative |

Abbreviations:
PLE, PICI-like element;
Sm$^R$, streptomycin resistance

Example 2. Bacteriophage Preparation

High-titer stocks of the ICP phages were prepared by growth on agar plates followed by polyethylene glycol (PEG) precipitation. Briefly, each phage was grown with the appropriate *V. cholerae* strain in soft agarose (LB broth supplemented with 0.3% agarose) overlays. Once confluent, overlays were incubated with STE buffer (100 mM NaCl, 10 mM Tris, 1 mM EDTA) overnight at 4° C. with gentle rocking to elute phage. The STE-phage solution was clarified by centrifugation, sterile-filtered, and incubated with 1× PEG (4% PEG 8000, 0.5 M NaCl) at 4° C. for 1-3 days to allow for phage precipitation. Phages were harvested by centrifugation at 10,000×g for 15 min at 4° C. and the phage pellet re-suspended in STE buffer. Phages were titered by plaque assay, as previously described (Dutta et al. Ibid.).

Example 3. In Vitro Phage Killing Assay

Figure 1B:
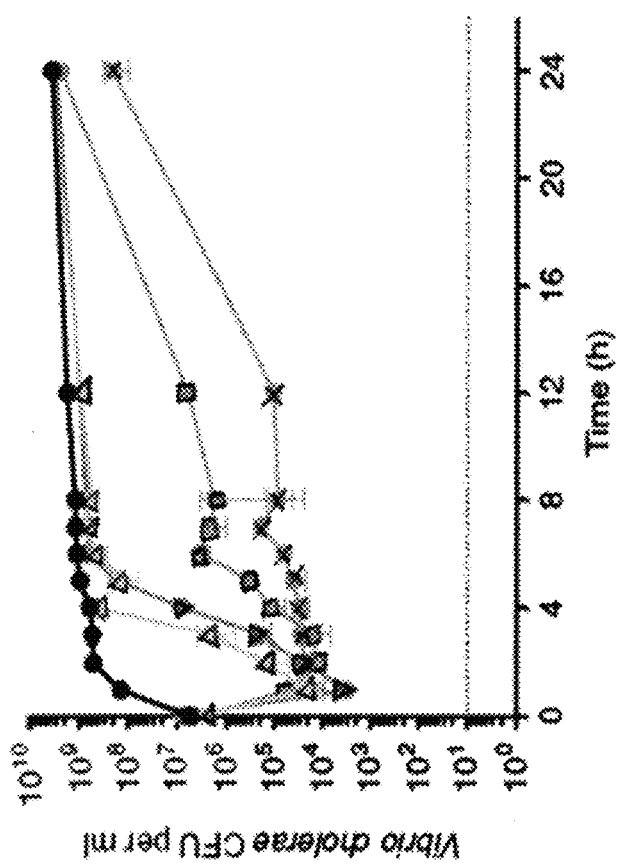
FIG. 1B shows the phage titer per ml in each of the cultures infected in FIG. 1A, as a function of time for 24 h. Phage titers persisted during the 24 h period, with final titers observed to range from about $10^6$ to about $10^8$ per ml.

Overnight cultures originating from single colonies of *V. cholerae* were diluted to an $OD_{600}$ of 0.05 in 50 ml LB supplemented with 100 μg/ml streptomycin (Sm) and grown at 37° C. with aeration. After 15 min, phages were added to each culture. At the time-points indicated in FIG. 1B, samples were collected to measure each of CFU/mL and PFU/mL.

Example 4. Infection of Infant Mice with *Vibrio cholerae*

Animal experiments were performed in accordance with the rules of the Department of Laboratory Animal Medicine at Tufts University and the Institutional Animal Care and Use Committee. 4- and 5-day old CD-1 infant mice (Charles River Laboratories) were infected. Each group of mice included animals from at least two different litters. Both male and female animals were used in this study. There was no observable correlation between sex of the animal and outcome of each experiment. The mice were not tested for the presence of resident *V. cholerae* phages as the animals had not previously been exposed to *V. cholerae* and accordingly would not harbor any *V. cholerae*-specific phages in their microbiome.

Infant mice in phage-treated groups were orogastrically dosed by oral intubation with phage diluted in 2.5% sodium bicarbonate. Infant mice in cholera treated groups received about $10^5$ CFU ("normal" infectious dose), or about $10^9$ CFU ("high" infectious dose), of *V. cholerae* diluted in 2.5% sodium bicarbonate. As phage preparations were administered at least three hours before bacteria, a theoretically calculated MOI would not be an accurate measure of the interaction between phage and bacteria. Instead, the titers of bacteria and phage inoculated into animals were calculated from the input materials, and the ranges therefore were expressed as the input number of phage, or the observed outcomes at conclusions of each example. For example, mice were sacrificed 24 hours post-infection, small intestines were dissected and homogenized in LB broth supplemented with 20% glycerol, and for assay of contents of cells the homogenates were serially diluted and plated on LB agar supplemented with 100 μg/mL Sm and the CFU per small intestine was calculated. To extract phage from small intestine homogenates, an aliquot of the intestinal homogenate was treated with chloroform and centrifuged at 10,000×g for 5 min. The supernatant was collected and used in plaque assays to allow for calculation of PFU per small intestine. To assess the resistance profile of *V. cholerae* cells that survive phage prophylaxis, up to 10 colonies per animal were randomly picked and efficiency of plating titer of each phage strain ICP-1, ICP-2 and ICP-3 was determined for each colony.

Example 5. Infection of Infant Rabbits with *Vibrio cholerae*

Infant three-day old New Zealand White rabbits (Charles River Laboratories) were used in this study. Each group of rabbits contained animals from at least two different litters and both male and female animals were included. There was no observable correlation between sex of the animal and outcome of each experiment. Infant rabbits in phage-treated groups were orogastrically dosed with phage diluted in 2.5% sodium bicarbonate. Three hours before infection with *V. cholerae*, infant rabbits were pre-treated with ranitidine hydrochloride to reduce stomach acidity (Caraco Pharmaceutical Laboratories) by intraperitoneal injection (2 μg per gram body weight). Infant rabbits were infected with $5 \times 10^8$ CFU *V. cholerae* AC53 diluted in 2.5% sodium bicarbonate. As for the mice examples, titers of bacteria and phage preparations to be inoculated into the subjects were calculated from titers of preparations and appropriate dosages. Animals were weighed at the start of the example, and periodically throughout the course of the infection. Percentage body weight was calculated by dividing body weight at the end of the infection period by bodyweight at the start. Animals were sacrificed 12-20 hours post-infection.

Infant rabbits that suffer from cholera typically lose 10-15% of their body weight within 12-14 hours and are sacrificed at this time. Infant rabbits that lose less than 10% of their body weight are sacrificed 20 hours post-infection, in accordance with our IACUC protocol. This time restriction is necessary as infants cannot be placed back with their mother after *V. cholerae* infection due to culling behavior and so are without food for the infection period.

After dissection, the intestines of each rabbit were homogenized in LB broth supplemented with 20% glycerol. Cecal fluid, if present, was collected with a 1 ml syringe. Cecal fluid and intestinal homogenates were serially diluted and plated on LB agar containing 100 µg/ml Sm for calculation of CFU per intestine. Phages were harvested from homogenates as described for infection of infant mice. Surviving *V. cholerae* colonies were colony-purified and assessed by efficiency of plating assays for resistance to ICP phages.

Example 6. Efficiency of Plating Assays

Efficiency of plating (EOP) assays were performed for isolates that survived phage predation. Each phage was titered on the isolate, on AC53 and also a phage-resistant strain as a negative control (ΔwbeL AC4653 for ICP-1 and ICP-3, and ΔompU AC2846 for ICP-2). The EOP was calculated by dividing the titer of the phage on the animal isolate by the titer of the phage on AC53. The limit of detection was $1 \times 10^{-6}$. Isolates were described as resistant if the EOP was observed to be less than about $1 \times 10^{-6}$, isolates were described as sensitive if the EOP was observed to be greater than about $1 \times 10^{-1}$, and isolates were described to be partially sensitive if the EOP was observed to be between these values.

Example 7. Sequence Analysis of Phage-Resistant Isolates

*V. cholerae* genomic DNA was extracted using a DNeasy Blood & Tissue Kit (Qiagen). Whole-genome libraries were prepared for single-end 150-bp sequencing using the Nextera XT DNA Library Preparation Kit (Illumina). Sequencing was conducted at the Tufts University Core Facility using an Illumina HiSeq 2500. Genomes were assembled using CLC Genomics Workbench 8 software and aligned to the *V. cholerae* O1 N16961 (Seed et al. *mBio* 2, e00334-00310, 2011) reference genome. To determine the mutations that may confer phage resistance, variant analysis was performed on mapped reads with a frequency threshold of 20%. Results were compared to AC53 variants (Seed et al. *PLoS Pathog* 8, e1002917, 2012) to remove those found in the wild-type inoculum. A surviving isolate that was determined to be sensitive to all three ICP phages was sequenced, and resulting variants were also removed from resistant isolates variant analyses.

Example 8. The Three-Phage ICP Cocktail Kills *V. cholerae* In Vitro

Since the first reports of lytic phages in cholera stools 86 years ago, there have been only anecdotal or correlative reports of the effects of such phages on cholera infections or on the dynamics of cholera out-breaks (d'Herelle et al. 1927, Ibid.; Faruque et al. *Proc. Natl Acad. Sci. USA* 102, 1702-1707, 2005; Faruque et al. *Proc. Natl Acad. Sci. USA* 102, 6119-6124, 2005). However, only recently have reports appeared of results of controlled experiments that test the effects of lytic phage on *V. cholerae* infection, and molecular analysis of phage strains (Zahid et al. *Infect Immun* 76: 5266-5273, 2008; Nelson et al. *PLoS ICP-2*. 4, e1000187, 2008. PMCID: PMC2563029; Seed et al. *mBio*. 2(1). pii: e00334-10, 2011. PMCID: PMC3037004; Seed et al. *Nature*. 494(7438):489-91, 2013. PMCID: PMC3587790). None of these studies have demonstrated prophylaxis resulting from administering phage to subjects prior to infection.

A variety of assays are used herein to obtain a set of natural lytic phage/*V. cholerae* pairs from rice-water stools. In general, lytic phages were isolated from rice-water stools and are found to interfere with *V. cholerae* infection of the small intestine. ICP-1 phage co-administered with a challenge of bacteria reduced the load of *V. cholerae* in the small intestine of infant mice in a dose-dependent manner (Nelson et al. *PLoS ICP*-2. 4, e1000187, 2008. PMCID: PMC2563029). However, it is not known if this inhibitory effect is characteristic of other lytic phages that associate with epidemic *V. cholerae* strains, and no prophylaxis was demonstrated. Indeed, it may be that some lytic phage have evolved to refrain from over-predation during intestinal infection, so that *V. cholerae* can establish infection, replicate to high enough density to cause cholera, and allow for continued propagation of phage, and for dissemination both of phage and host bacterial cells back into the environment.

Initial in vitro killing time-course analyses indicated that a three-phage ICP cocktail was more effective in killing *V. cholerae* than each individual phage (FIG. 1A). Cultures of host strain, infectious pathogenic *V. cholerae* E7946 (AC53) were grown in the following culture conditions: the absence of phage (control); or in the separate presence of each lytic bacteriophage strain ICP-1, ICP-2, and ICP-3, or in the presence of the ICP cocktail, at a multiplicity of infection (MOI) of 1 for each phage and bacterial mix. Bacteria (FIG. 1A) and phage (FIG. 1B) titers were enumerated every hour for eight hours, and at 12 and 24 hours.

The data show that the bacterial population declined in all conditions of phage infection initially, and that growth resumed for cultures grown in the presence of ICP-1 or ICP-3 within four to six hours, respectively (FIG. 1A). Cells incubated in the presence of ICP-2 resumed growth more slowly, and reached the same density as the control within 24 hours.

In contrast, cells grown with the ICP cocktail did not reach the same density as the no-phage control by the end of the experiment. Phage titers dropped and remained stable for all conditions over the course of the example (FIG. 1B). *V. cholerae* was able to escape phage predation over time, given that the starting bacterial inoculum was high ($5\times10^7$ CFU) and likely contained phage-resistant mutants that had been positively selected during the time course of the liquid culture.

Example 9. *V. cholerae* Colonization of the Infant Mouse Small Intestine is Reduced by the ICP Phage Cocktail Because genotypic and phenotypic variability are high for phage strains and their host bacteria, a strategy used herein is to restrict analysis to naturally occurring lytic phage/*V. cholerae* cocktails isolated from rice-water stools. Population dynamics are determined over the course of infection for three such pairs previously isolated from different patients in Bangladesh (Nelson et al. *PLoS ICP*-2. 4, e1000187, 2008. PMCID: PMC2563029; Seed et al. *mBio.* 2(1). pii: e00334-10, 2011. PMCID: PMC3037004). The percentage of *V. cholerae* in the rice-water stools that are resistant to the phage present was determined. This analysis uses archived samples of rice-water stools containing lytic phage and *V. cholerae*. The three phages used herein, ICP-1, ICP-2 and ICP-3, were previously analyzed by sequencing and determination of host range (Seed et al. *mBio.* 2(1). pii: e00334-10, 2011. PMCID: PMC3037004).

The ICP cocktail was observed herein to be more effective in vitro than each phage strain alone in killing *V. cholerae*.

To test if this might be true in vivo, prophylaxis experiments were performed in the infant mouse model of *V. cholerae* colonization. The ICP cocktail was tested to determine whether it would be effective in preventing *V. cholerae* infection of the infant mouse small intestine. Mice were divided into five groups and received either no phage (control), or each individual phage strain of ICP-1, ICP-2, and ICP-3, or the mixture of all three phage strains which is referred to herein as the ICP cocktail (or the phage cocktail or the bacteriophage cocktail).

Mice were administered the phage preparations in a dose of between about $1\times10^6$ and $1\times10^7$ PFU by orogastric inoculation 3 hours prior to infection with $5\times10^5$ colony-forming units (CFU) *V. cholerae*. After 24 hours, mice were sacrificed and *V. cholerae* and phages in the small intestine enumerated.

Figure 2A:
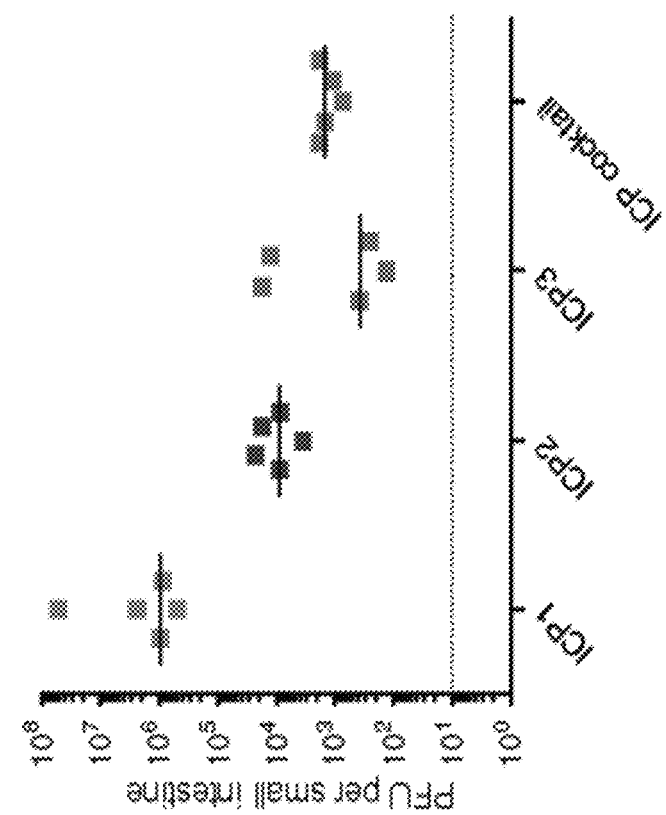
FIG. 2A is a graphical representation showing reduction of numbers of viable *V. cholerae* bacteria (CFU) present in small intestines of infant mice administered each one of the indicated phage strains or administered the cocktail of three strains, compared to a control of mice not administered phage. Phage were administered at a dose of between about $10^6$ to about $10^7$ PFU. It was observed that the cocktail of three strains reduced bacterial titers more than five orders of magnitude down to the limits of detection (about 10 colonies), and that each of the individual strains reduced the bacterial load to between two to five orders of magnitude.

The number of surviving *V. cholerae* cells in the small intestine was observed to have been reduced by at least two orders of magnitude in all conditions in which phage was administered, in comparison to the non-treated no phage control. Among the individual single strains administered, ICP-3 was observed as the most successful single phage for reducing or eliminating bacterial cells as judged by huge reductions in numbers of CFUs (three to six orders of magnitude reduction) (n.s). See, FIG. 2A.

The ICP cocktail was observed to be more effective than any of the individual strains, with no *V. cholerae* detectable in the intestinal homogenates of 4 out of 5 mice (P<0.01).

Figure 2B:
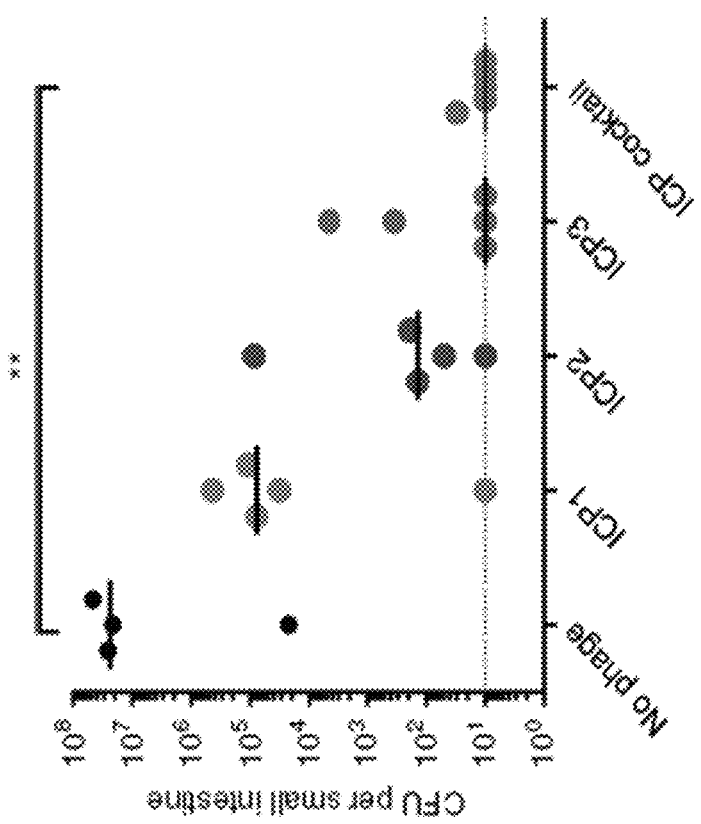
FIG. 2B is a graphical representation of titers of phage in the small intestines of animals of FIG. 2A infected with *V. cholerae*.

These data show that, in comparison to each phage strain individually, the ICP cocktail of three strains was superior at preventing *V. cholerae* colonization. Phage number as PFUs were still present in the small intestine at the end of the time period (FIG. 2B), indicating that these phages can survive and persist in the intestinal tract to continue to confer protection against the bacterial pathogenic cells.

To determine whether the bacteriophage cocktail is a more general preventive measure than each strain administered individually, the ICP cocktail was tested for effectiveness when administered up to 24 hours before *V. cholerae* infection. To determine if phage survive in the small intestine for long periods of time in the absence of the host bacteria, mice were dosed with phage (between $3\times10^7$ and $3\times10^8$ PFU) by oral gavage and sacrificed after 3, 6, 12, or 24 hours. Phage titers from intestinal homogenates were determined using plaque assays (FIG. 3A). After 3 hours, the phage titers for ICP-1 and ICP-3 were observed to have remained stable, while ICP-2 titers had dropped approximately 10-fold. For all three phage strains, titers dropped only 10- to 100-fold after 6 to 12 hours. After 24 hours, ICP-1 and ICP-2 were still retained at approximately $10^5$ PFU per small intestine, and the titer of ICP-3 fell to between $10^2$ and $10^4$ PFU per small intestine. These data further show that a substantial number of the ICP phages were able to survive in the intestinal tract for at least 24 hours in the absence of cells of the host bacterium, pathogenic *V. cholerae*.

To test an extent of phage protection if administered several hours prior to exposure to *V. cholerae*, infant mice were inoculated with the ICP cocktail at a time 6, 12 or 24 hours before challenge with between $5\times10^5$ or $9\times10^5$ CFU *V. cholerae*. Animals in a negative control group were not treated with phage. The data in FIG. 4B show that the 6-hour prophylaxis was most successful; the number of surviving *V. cholerae* cells was reduced at least three orders of magnitude, in comparison to the no phage control group, with no detectable *V. cholerae* observed in four of the seven mice that received phage (P<0.0001). The number of *V. cholerae* cells was observed to be significantly lower for the 12-hour group (P<0.001), with four of these animals having no detectable *V. cholerae* at the end of the experiment. The number of *V. cholerae* cells was also reduced two orders of magnitude in the 24-hour group. Furthermore, lytic phage PFUs were detectable 24 hours post-infection (FIG. 3C).

To determine if the ICP cocktail would limit colonization if mice were treated with a higher challenge of pathogenic bacteria, infant mice were inoculated with $1\times10^8$ CFU of *V. cholerae*, a dose approximately 200-fold higher than in FIGS. 3B and C. The data in FIG. 3D show that the ICP cocktail was effective to significantly reduce *V. cholerae* colonization of the small intestine by at least two orders of magnitude in mice administered phage at either 6, 12, or 24 hours prior to challenge. Phage PFUs were detected at 24 hours post-infection at similar levels in all three phage-treated groups (FIG. 3E). In concert, these data indicate potential use of a phage prophylaxis approach to prevent *V. cholerae* colonization of the small intestine.

*V. cholerae* bacteria were isolated from intestinal homogenates of several of the mice dosed with the ICP cocktail (FIGS. 2 and 3). Due to the complexity of infection within the gut, it is possible that these bacteria survived merely because they did not encounter the ICP phages. Alternatively, these cells could contain genetic mutations that allowed them to escape phage predation.

Example 10. The ICP Cocktail Provides Protection in the Infant Rabbit Model of *V. cholerae* Infection To assess the ability of the ICP cocktail to prevent cholera in further mammalian model systems, an animal model with infant rabbits was used. In contrast to infant mice, infant rabbits infected by *V. cholerae* develop the profuse secretory diarrhea associated with cholera (Abel et al. *Current protocols in microbiology* 38, 6A 6 1-15, 2015). To establish if phages could be retained in the rabbit intestinal tract in the absence of *V. cholerae*, animals were dosed with the ICP cocktail alone ($3\times10^8$ PFU). After 3 or 24 hours, the animals were sacrificed and phage titers were determined from intestinal homogenates.

It was observed that even after 24 hours, $10^6$ phages were recovered from each intestine (FIG. 4A). To determine if the ICP cocktail could block infection by *V. cholerae*, phages (between $4\times10^9$ and $8\times10^9$ PFU) were orogastrically administered to two groups of infant rabbits either 3 or 24 hours prior to challenge with $5\times10^8$ CFU *V. cholerae*. A control group did not receive phage. Animals were monitored for signs of cholera, specifically weight loss (FIG. 5) and the presence of rice-water stool (also referred to here as cholera-like diarrhea). The no-phage control group were observed to have cholera-like symptoms 12 to 14 hours post-infection, in line with previously published observations (Abel et al. *Current protocols in microbiology* 38, 6A 6 1-15, 2015), and were sacrificed at this time point. The cecum of each infected rabbit was observed to be distended and to contain approximately 0.5 to 1 ml of accumulated fluid, which are further indicia of *V. cholerae* infection. Approximately $10^9$-$10^{10}$ CFU of bacteria were enumerated from cecal fluid and these homogenates of intestine of each animal (FIG. 3B) from this group.

*V. cholerae* were not detected in the tissues of four of the seven rabbits that had been administered ICP cocktail 3 hours prior to infection (FIG. 4B), indicating that these animals were cleared of the infection by the treatment. Between $10^6$ and $10^8$ CFU of *V. cholerae* were obtained from intestinal homogenates from the remaining three rabbits in this group, which was calculated to have been a 10- to 100,000-fold decrease in comparison to the non-treated group (FIG. 4B, P<0.001). Between approximately $10^5$ to $10^9$ CFU of *V. cholerae* were counted from each intestine of animals administered phage 24 hours before infection (FIG. 4B), presenting a 10- to 100,000-fold decrease in bacterial load compared to control animals not administered phage (P<0.05).

Example 11. *Vibrio* Mutants Resistant to Three Phage Strains did not Arise in Treated Infant Mice To determine the phage resistance phenotypic profile of surviving cells, *V. cholerae* colonies obtained from the examples in FIGS. 3B and 3C were randomly selected for colony purification. Bacterial cultures were obtained from the isolated colonies, and were used in efficiency of plating (EOP) assays to characterize the isolates with respect to resistance phenotype. The results are shown in Table 3, see also Yen et al., Ibid., 2017, Supplementary File 1, Table S1 and detailed in Supplementary File 2, Table S3, the data for which are incorporated herein by reference.

To determine whether *V. cholerae* that survived phage prophylaxis were sensitive or resistant to the ICP phages, *V. cholerae* isolates from each of the mouse and the rabbit intestinal homogenates were randomly selected for colony purification, and phage resistance phenotype of isolates was measured by efficiency of plating (EOP) assays (Yen et al., Ibid.) in which sensitivity is defined as an efficiency normalized to the parent wild type *V. cholerae* which is greater than 0.1; partial sensitivity is defined as 0.1 to 1e; and resistance is an EOP of less than $10^{-6}$.

These data conclude that 100% of the colony isolates from mice that received the ICP cocktail 6 or 12 hours prior to challenge were sensitive to all three ICP phages. The majority of isolates from mice given the ICP cocktail 24 hours prior to challenge were observed also to be sensitive to all three ICP phages; however, a small number showed differing ICP resistance phenotypes. None were observed to be resistant to all three phage strains.

Most important, the fact not finding substantial numbers of isolates from the infant mice intestines which could be characterized as resistant to all three ICP phage, indicates that the cocktail mix is a suitable therapeutic agent for continued prevention of infection.

TABLE 3

Phage resistance of *V. cholerae* isolates generated from phage prophylaxis in the infant mouse

| | Length of Prophylaxis | | |
|---|---|---|---|
| Resistance Class | 6 h (n = 30) | 12 h (n = 50) | 24 h (n = 99) |
| S to all ICP | 30 (100%) | 50 (100%) | 75 (81%) |
| R to ICP-1 only | — | — | — |
| R to ICP-2 only | — | — | 14 (14%) |
| R to ICP-3 only | — | — | 2 (2%) |
| PS to ICP-2 only | — | — | 4 (4%) |
| ICP-1 (PS) and ICP-3 (PS) | — | — | 1 (1%) |
| ICP-1 (PS) and ICP-3 (R) | — | — | 3 (3%) |
| ICP-1 (R) and ICP-3 (PS) | — | — | — |
| R to all ICP | — | — | — |

Table 3 shows results from isolates obtained from intestinal homogenates of phage cocktail treated infant mice seen in FIG. 3, as a function of time period between treatment and challenge with the pathogenic bacteria. From intestinal homogenates of mice treated 6 h prior to pathogen challenge, 30 bacterial isolates were tested, of which 100% were sensitive to all three ICP strains. Similarly from mice treated 12 h prior to challenge, 50 isolates tested were entirely sensitive to all three ICP strains. From mice treated 24 h prior to challenge, 99 isolates were tested, of which 75 (81%) were sensitive to all three ICP strains. Only four isolates were resistant to two of the three ICP strains: one isolate had a phenotype of partial sensitivity to ICP-1 and ICP-3; three isolates showed partial sensitivity to ICP-1 and resistance to ICP-3. Most important, no isolates were observed which were resistant to all three phages.

Example 12. Genetic Basis of Bacterial Resistance to ICP Phage Strains

To determine the genetic basis for resistance, 24 isolates obtained from samples of animals from FIGS. 4B and 4C were analyzed by whole-genome sequencing followed by variant analysis (Heidelberg et al. *Nature* 406, 477-484, 2000; Lazinski et al. *BioTechniques* 54, 25-34, 2013). It was shown previously that slipped-strand mispairing in the poly-A tracts of O-antigen synthesis genes can result in abnormal O-antigen and confer ICP-1 resistance (Seed et al. *PLoS Pathog* 8, e1002917, 2012).

Mutations in ICP-1- and ICP-3-resistant isolates were found in O-antigen synthesis genes located on chromosome 1 of *V. cholerae* between open reading frames VC0240 (gmhD) and VC0264 (rjg) (Chatterjee et al. *Biochimica et biophysica acta* 1690, 93-109, 2004) (Supplementary File 3, Table S4). LPS mutations were a common source of resistance in these isolates; however, this is not of major concern because strains carrying such mutations have previously been shown to be avirulent (Kamp et al. *PLoS Pathog* 9, e1003800, 2013; Pritchard et al. *PLoS genetics* 10, e1004782, 2014; Fu et al. *Cell host & microbe* 14, 652-663, 2013). For examples, mutations in onipU and toxR confer ICP-2 resistance (Seed et al. *eLife* 3, e03497, 2014). Data herein show that mutations in ICP-2-resistant isolates were found in open reading frames VC0633 (ompU) or VC0984 (toxR) (Supplementary File 3, Table S4).

To determine the genetic basis for resistance, whole-genome sequencing and variant analysis were conducted on 36 isolates, chosen on the basis of their differing resistance phenotypes (Yen et al., Ibid.). Results obtained with isolation of strains with mutations found in ICP-1- and ICP-3-resistant isolates were similar to those observed from the mouse examples in FIG. 3. For 33 of these strains, mutations were observed in genes involved in O-antigen synthesis. For three strains, no mutations related to known phage-resistance strategies had been detected. It was concluded from these data in two animal models that the leading source of phage resistance is mutation of the genes required for production of the phage receptors.

Example 13. No Cholera Symptoms in Treated Infant Rabbits

Figure 5:
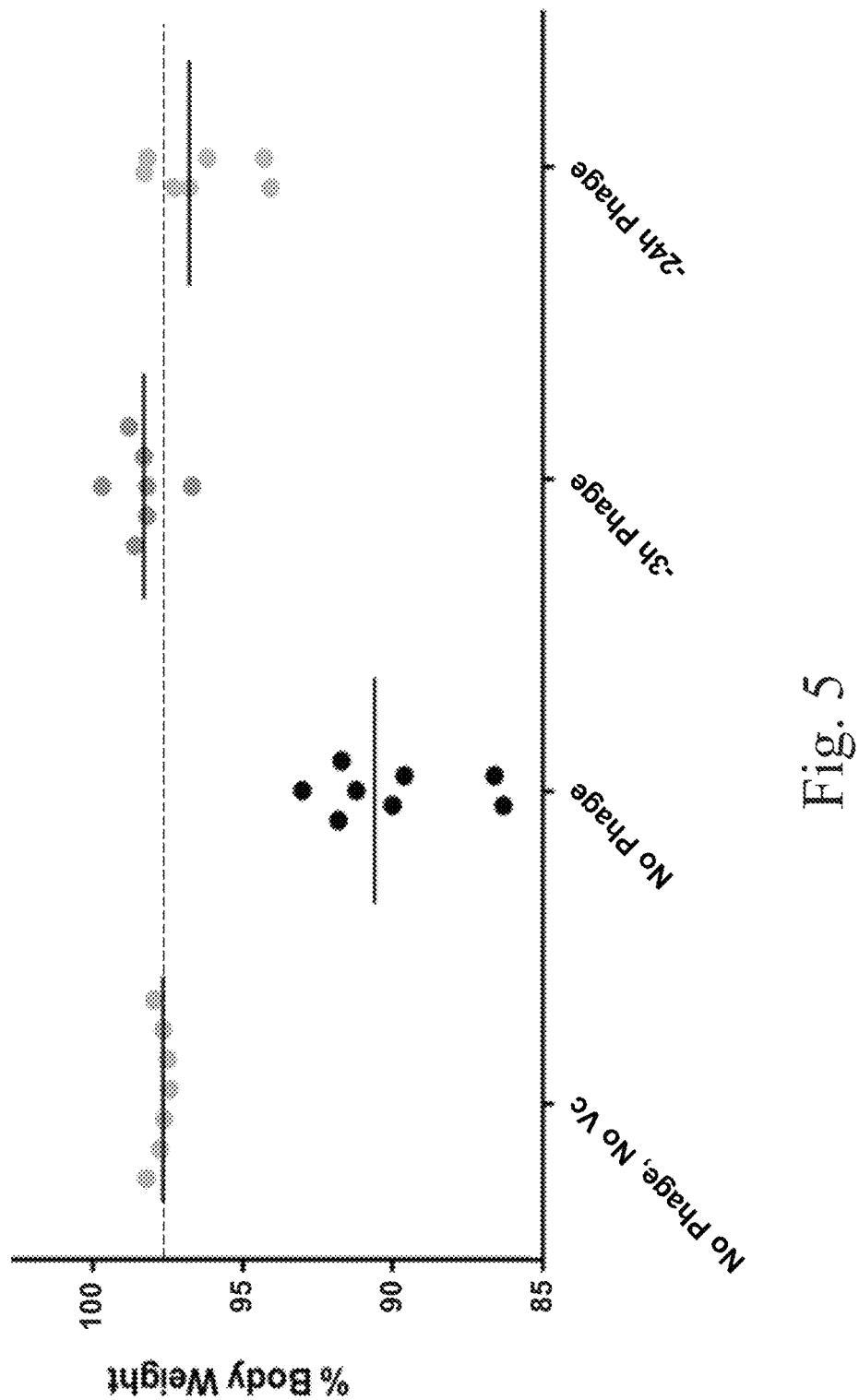
FIG. 5 shows percent of initial body weight of subjects by the end of the time course shown in FIGS. 4A-C. Subjects receiving phage cocktail prophylaxis either 3 h or 24 h prior to challenge with *V. cholerae* maintained a body weight comparable to those in the untreated controls (No Phage, No Vc), with prophylaxis 3 h prior to challenge being more effective than dosing at 24 h, with respect to maintenance of body weight following challenge with *V. cholerae*. In contrast, subjects infected with *V. cholerae* not treated with phage lost about 10-15% of body weight during the course of the example, which is a large loss of body weight for a short time period. A small weight loss in control animals occurred as a result of subject infant rabbits separation from their dams.
Figure 6:
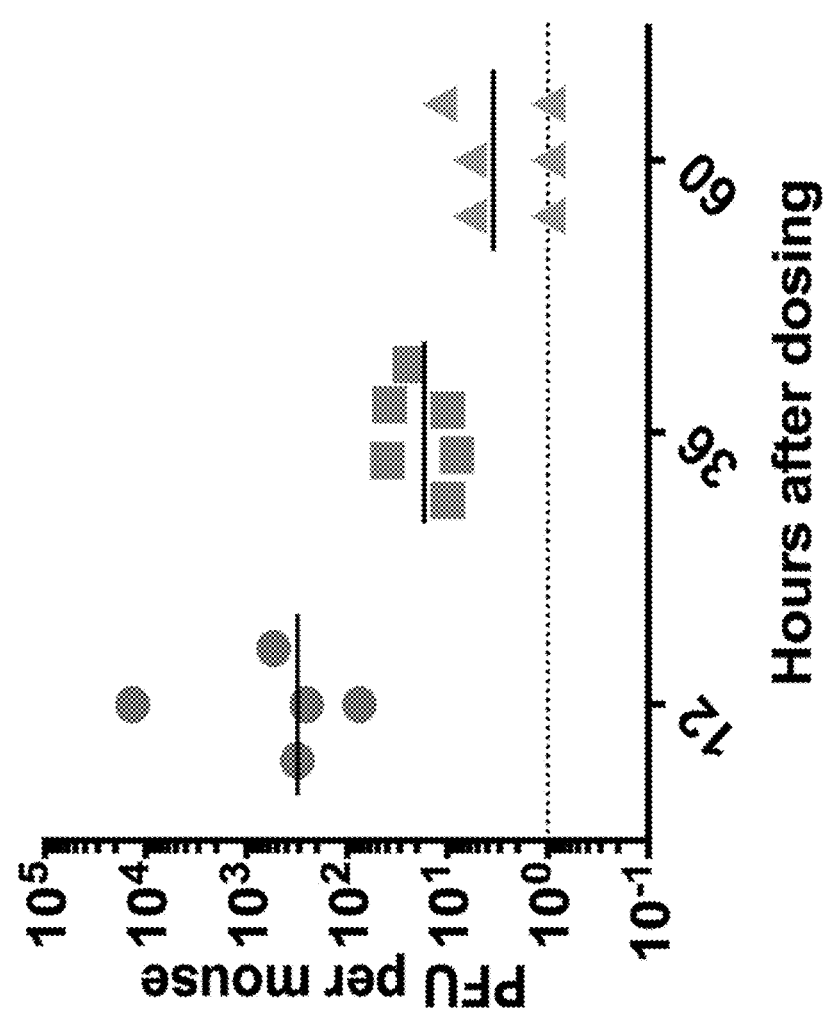
FIG. 6 is a determination of ability of phage to persist in an adult animal model. Phage cocktail was administered to mice, and stool samples taken at time points indicated were assayed for phage content. Phage were detectable at reproducible titers per subject at 12 h and 36 h, and up to 60 h following administration.

Most important, in addition to the decrease in the bacterial load observed in examples herein as a result of treatment of infant rabbits with the phage cocktail, no evidence of rice-water stool or significant weight loss was observed for rabbits in either of the phage-dosed groups up to 20 hours after *V. cholerae* challenge (FIG. 5). In contrast, control rabbits infected with *V. cholera* absent phage lost about 10% of body weight within 24 h.

Unlike mice, rabbits infected with *V. cholerae* are capable of producing many of the gastric symptoms of this disease observed in humans, including secretory diarrhea with an extended cecum. Accordingly, subjects in the different groups of treatment with phage cocktail and challenge with the pathogenic bacteria were further observed for signs of the disease, and cecal fluid was collected and volume measured.

Upon dissection of these animals, it was found that 0.1 ml of cecal fluid was present in only one subject (animal number 16, see Table 4), of the group of 10 that had been dosed with phage 24 hours before *V. cholerae* infection. None of the ceca of the other animals treated with the same cocktail for three hours, showed fluid accumulation. In contrast the challenged animals not treated with phage cocktail, but challenged with the bacterial pathogen all produced cecal fluid.

TABLE 4

Bacterial counts of collected cecal fluid from phage prophylaxis in the infant rabbit Cecal Fluid Bacterial Counts (CFU/ml)

| No Phage | | 3 hours | | 24 hours | |
| --- | --- | --- | --- | --- | --- |
| Animal 1 | $6.2 \times 10^8$ | Animal 9 | N/A | Animal 16 | $5.2 \times 10^5$ |
| Animal 2 | $3.9 \times 10^8$ | Animal 10 | N/A | Animal 17 | N/A |
| Animal 3 | $8.8 \times 10^8$ | Animal 11 | N/A | Animal 18 | N/A |
| Animal 4 | $7.8 \times 10^8$ | Animal 12 | N/A | Animal 19 | N/A |
| Animal 5 | $1.0 \times 10^8$ | Animal 13 | N/A | Animal 20 | N/A |
| Animal 6 | $1.1 \times 10^8$ | Animal 14 | N/A | Animal 21 | N/A |
| Animal 7 | $8.2 \times 10^8$ | Animal 15 | N/A | Animal 22 | N/A |
| Animal 8 | $9.2 \times 10^8$ | | | Animal 23 | N/A |
| | | | | Animal 24 | N/A |
| | | | | Animal 25 | N/A |

The cecal fluid was analyzed for presence of bacteria, as shown in Table 4. Fluid samples from animals not receiving phage cocktail all presented with high bacterial counts, from about $10^8$-$10^9$ CFU. It was concluded that phage cocktail-treated subjects did not produce symptoms of cholera, and that control animals not receiving the cocktail showed signs of the disease and bacterial presence in the ceca.

Approximately about $10^4$-$10^6$ to about $10^8$-$10^9$ PFU were collected from each intestinal homogenate of the phage-treated animals (FIG. 3C), indicating that phages persisted in the intestine over the course of the treatment and infection. These observations indicate that the ICP cocktail protected against the signs of cholera over the duration of the examples.

Example 14. Mutants Resistant to Three Phage Strains did not Arise in Rabbits

Colony isolates were obtained from rabbit intestine homogenates and were analyzed for presence of resistance mutations from groups treated 3 h or 24 h prior to challenge with the pathogenic bacteria. Quantitative criteria used were the same as for the mouse model system. Results obtained were similar to those obtained in the mouse model. No isolates were observed that had acquired mutations conferring resistance to all three phage strains. Of 20 isolates obtained from 3 h treated animals, 20% were observed to retain sensitivity to all three phage strains; one was resistant to ICP-1 only; none were resistant to ICP-2 only or to ICP-3 only. Small numbers of the isolates were partially sensitive to pairs of phage. See Table 5.

TABLE 5

Phage resistance of *V. cholerae* isolates generated from phage prophylaxis in the infant rabbit

| | Length of Prophylaxis | |
| --- | --- | --- |
| Resistance class | 3 h (n = 20) | 24 h (n = 76) |
| S to all IP | 4 (20%) | 30 (39%) |
| R to ICP-1 only | 1 (5%) | 2 (3%) |
| R to ICP-2 only | — | — |
| R to ICP-3 only | — | — |
| ICP-1 (PS) and ICP-3 (PS) | 2 (10%) | 2 (3%) |
| ICP-1 (PS) and ICP-3 (R) | 2 (10%) | — |
| ICP-1 (R) and ICP-3 (PS) | 3 (15%) | 8 (11%) |
| ICP-1 (R) and ICP-3 (R) | 7 (35%) | 30 (39%) |
| R to all ICP | — | — |

Collectively these data indicate that the phage cocktail is both efficient at killing *V. cholerae* cells in two different mammal systems in vivo, and reduces or prevents *V. cholerae* colonization of the intestine. The phage cocktail of three different phage strains provides protection also against the onset of cholera-like diarrhea in the infant rabbit model of cholera infection. Furthermore, isolates shed by the animal that were resistant to one or two of the ICP phage strains were observed to have avirulent mutations, as described of O1-antigen mutants (Seed et al. *PLoS Pathog* 8, e1002917, 2012).

These data show that prophylactic administration of a *V. cholerae*-specific phage cocktail is protective against cholera, by reducing both colonization in two animal models and cholera-like diarrhea in the rabbit animal model. The ICP cocktail successfully killed *V. cholerae* in vitro, prevented colonization of the infant mouse, and precluded the onset of cholera-like diarrhea in the infant rabbit. While *V. cholerae* could be isolated from intestinal homogenates of some phage-treated animals, the surviving population was consistently smaller by orders of magnitude. It is important to note that many mutations identified that confer resistance to the ICP phages likely result in a loss of virulence for *V. cholerae*. Crucially, at the end of the time courses of examples herein, the bacterial population remained sensitive to at least one of the three ICP phages. The effectiveness of the ICP cocktail in killing *V. cholerae* cells was at least in part a function of the concentration of phages that were in the intestine at the time of *V. cholerae* infection.

Example 15. Phage Cocktail does not Disrupt the Composition of Intestinal Microbiota Normal human microbiota do not include cells of *V. cholera*. It is likely that phage receptors are highly specific to interactions with structures on the surface of a host particular genus or species of bacterium. It is an advantage of the present invention, therefore in contrast to antibiotic therapeutics that are capable of wiping out the entire microbiome of a subject, that a therapeutic agent which is a mixture or cocktail of three specific bacteriophage strains would have no effect on the unrelated bacterial genera or species that constitute a part of the normal human (or mouse or rabbit) microbiome.

To test the specificity of the ICP phage strains on intestinal microbiota in an adult animal model, mice were dosed with phage cocktail, or with antibiotics or heat-killed phage cocktail. Stool samples were collected for several days before dosing. FIG. 6 shows that phage persisted in adult intestine for at least 60 hours.

Further analyses were undertaken to determine whether phage cocktail treatment of subjects would have any effects on microbiome compositions. Genomic DNA was extracted from stool samples stored frozen and used as template for PCR with 16S V4 region specific primers. PCR products were purified, and Nextera sequencing adapters added by PCR. Samples were analyzed using a 250 bp paired end Illumina MiSeq run, and data were analyzed using QIIME v1.8. Operational Taxonomic Units were picked by 99% similarity, and phylogeny was assigned using the Greengenes database.

Figure 7:
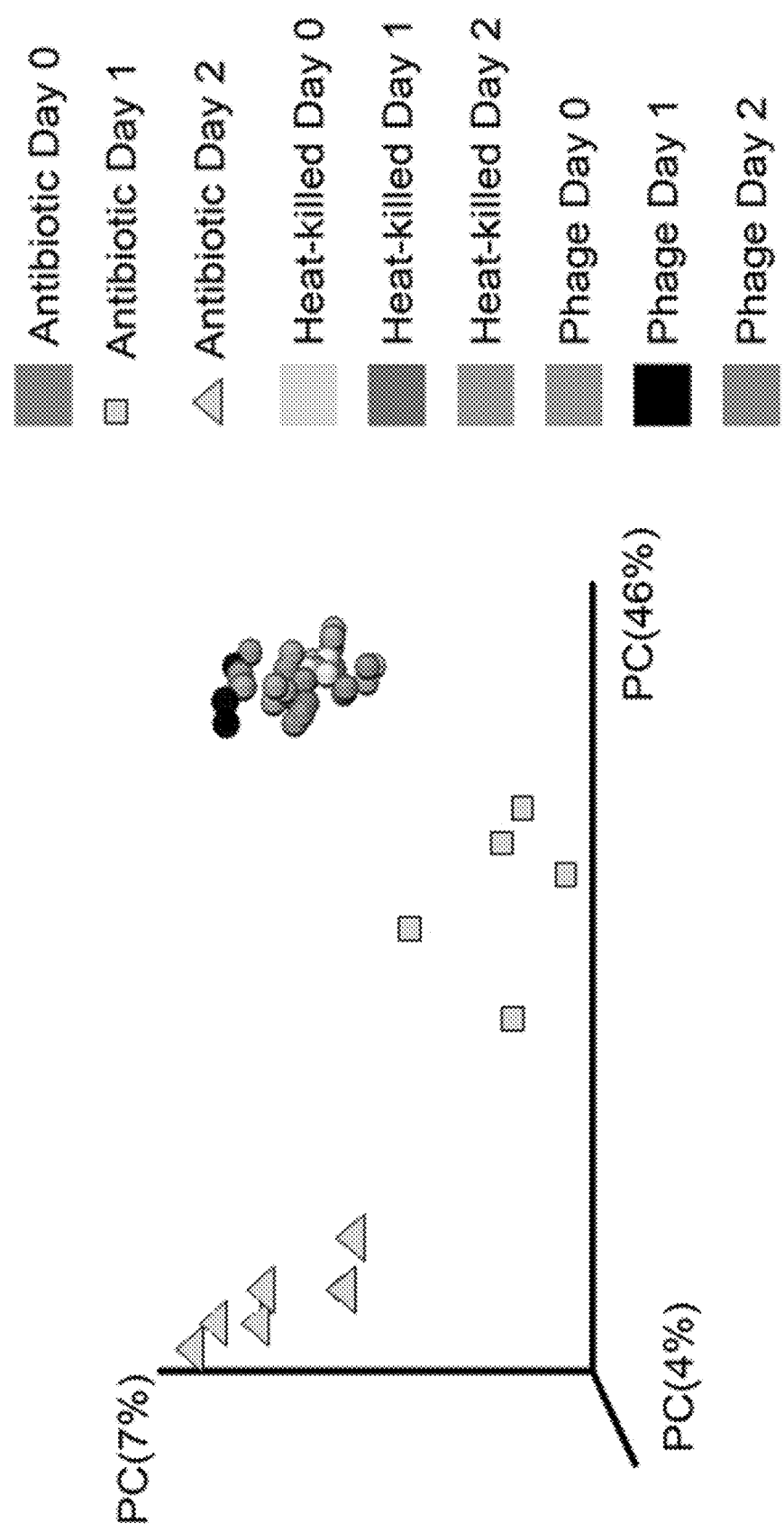
FIG. 7 is a principal coordinate analysis of beta-diversity of samples from FIG. 6, of genomic DNA extracted from stool samples taken at day 0 (immediately prior to treatment) and day 2 (approximately 36 h after treatments) in stools of animals treated with antibiotics (positive control), or with phage cocktail, or with heat-killed phage cocktail (negative control). Genomic DNA was used as a template for PCR with 16 s V4 region specific primers. PCR products were purified, Nextera sequencing adapters added by PCR, and samples were sequenced using a 250 bp paired end Illumina MiSeq run. Data were analyzed using QIIME v1.8. Operational taxonomic units (OTUs) were picked by 99% similarity and phylogeny assigned using the Greengenes database. Each point represents the intestinal microbial population from one animal. The data show that microbiomes of animal groups following antibiotic treatment were dissimilar between day 0 and day 1, and between day 1 and day 2. In contrast, there was no dissimilarity in the microbiomes of subjects in the phage cocktail treated and heat killed phage cocktail treated control animal groups between any of these days. These results indicate that phage treatment did not affect microbiota composition.

Beta-diversity of samples is shown in FIG. 7, using principal components analysis. This analysis calculates the phylogenetic distance between pairs of samples, acting as a similarity score between populations. The data in FIG. 7 show that the microbiome populations of phage cocktail treated subjects and controls (receiving heat-killed phage cocktail) are highly similar. Dissimilarity was observed for positive control animals: two groups of samples obtained from antibiotic treated animals (six dots close to the left axis which animals had been treated for two days with antibiotics; and a group of five dots close to the bottom axis which animals had been treated for one day with antibiotics).

Figure 8:
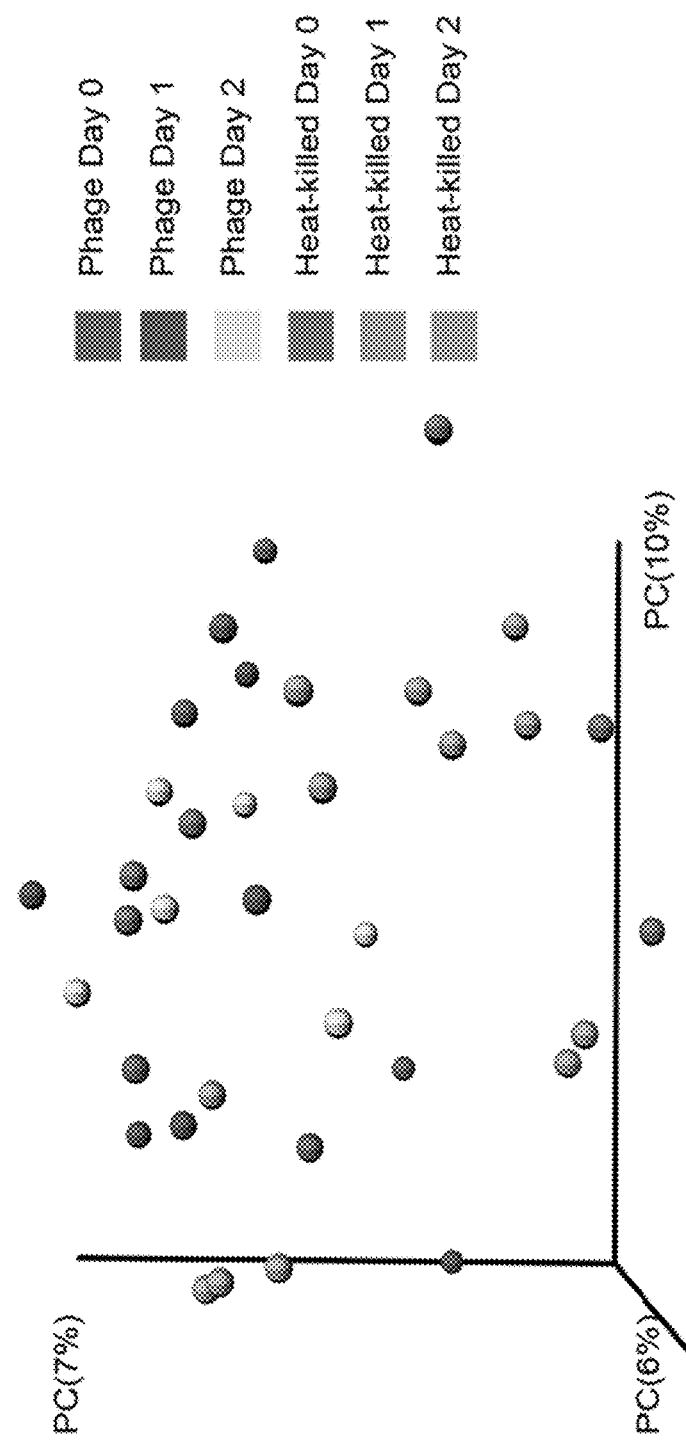
FIG. 8 shows an analysis of the same data as FIG. 7, omitting the antibiotic samples. The differences in the amount of beta diversity between the samples is much lower than in FIG. 7, and there is no discernable pattern of dissimilarity among any of the groups, further indicating that phage treatment did not affect the microbiota composition.

These data show that the intestinal microbiota in subjects treated for one or two days, with the phage cocktail regardless of heat killing of phage (control), are similar in composition, so that no disruption of the microbiota was a result of the phage cocktail administration. In another analysis of data which included removing the antibiotic treated sample data (FIG. 8), the analysis shows that the extents of relatedness of microbiomes from different stool sample bacterial populations were similar in stools from animals treated for zero days, treated for one day, or treated for two days, and that the presence of either live or heat killed phage cocktail of three phage strains had no effect on the extent of relatedness. FIG. 8 shows these data points plotted omitting the samples from antibiotic-treated animals. There is no clustering of samples and the largest spread is on the abscissa, which is 10%, compared to 46% on FIG. 7. Since the data here are interspersed and show no difference in clustering for live phage treatment compared to controls for heat killed phage, these data confirm that phage treatment does not affect the microbiome and that the cocktail is host specific for *V. cholerae* bacterial cells.

These data show that the phage strains which were present in the cocktail and used for prophylaxis of subjects, are specific for infection and killing of pathogenic *Vibrio* bacterial cells, as these strains did not infect and alter the population distributions of non-*Vibrio* species of bacteria characteristic of normal intestinal microbial populations.

Example 16. The Phage Cocktail is Effective in a Wide Range of Ratios of Component Strains The ratios of numbers of virions of each phage strain of the ICP-1, ICP-2 and ICP-3 used in preparation of the most effective cocktail were varied to determine optimum relative amounts. The additional ratios of the three phage strains that were tested, and compared to data above using a ratio of 1:1:1 of the number of input phage from each of the three ICP strains for ICP-1:ICP-2:ICP-3 were: 1:1:10; 1:10:1; 10:1:1; and 1:5:10. These examples test potential optimization of the ratio, if whether variations in phage receptors on the host bacterial pathogen, and relative kinetics of phage strain adsorption, burst time and burst size, might influence extent of bacterial killing and maximal phage persistence. In this example, the range of MOIs for any two of the three phage stains was varied through a range of two orders of magnitude differences (1:10 compared to 10:1) in the ratios.

Figure 9A:
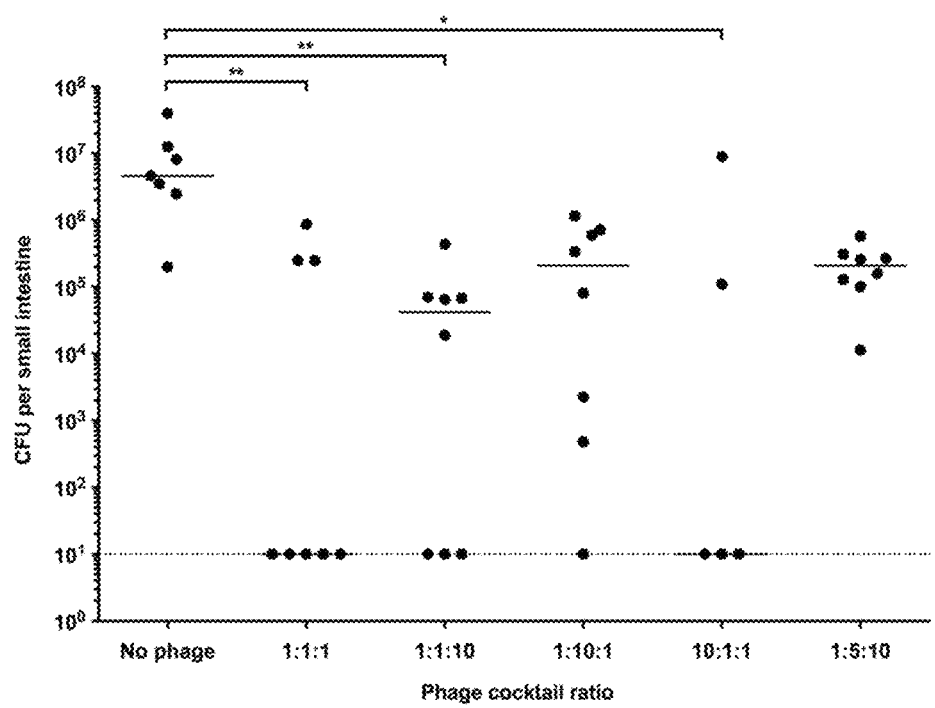
FIGS. 9A and 9B are graphical representations of CFU assays from the infant mouse small intestine model as in FIG. 3A.
Figure 9B:
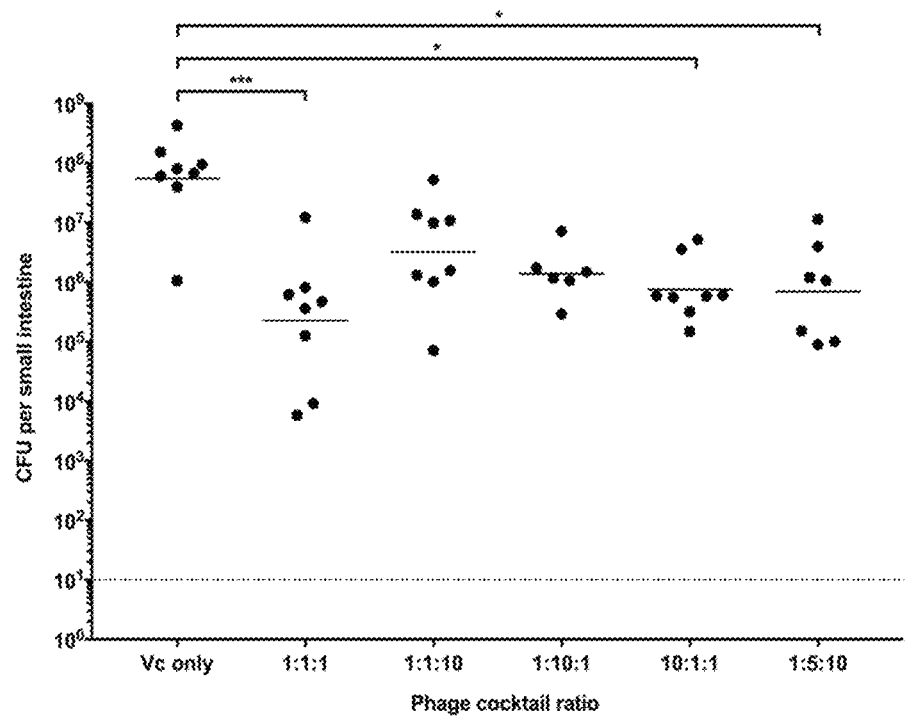

The data in FIGS. 9A and 9B for two different challenge amounts of *V. cholerae*, using the infant mouse model of FIGS. 3B and 3D above, indicated that all the ratios were effective in prophylaxis, and all gave results of reduction in numbers of pathogenic bacteria in the gut similar to those obtained herein with a ratio of 1:1:1. Thus compared to control subjects not treated with phage, the phage cocktails reduced the bacterial load completely in some subjects to within limits of detection, and in other subjects about two orders of magnitude. These data indicate that the phage strains herein are similar in kinetics of affinity for the bacteria, burst size, burst time, and other features of phage life cycle.

Furthermore, as complete reduction of the bacterial load was observed with animal model systems at shorter prophylaxis times in examples herein, optimization of the timing for each dose is analyzed before entry into clinical trials for human use. As an individual living in an environment of endemic cholera may be repeatedly exposed to *V. cholerae*, multiple doses are prescribed to control the infection in each individual, up to a point at which it is completely eradicated in that individual, and even in the population.

Current phage therapy research is focused on treating ongoing infections. Results herein indicate the potential of phage therapy in preventing infections. The data presented herein show that the promise to prevent cholera warrants further investigation, with compositions and methods of using a phage cocktail as shown herein having a plurality of phage strains with at least two different types of phage receptor for interactions with the pathogenic bacteria. A rapid-acting phage prophylaxis approach is useful in at-risk individuals, such as the household contacts of individuals who display cholera symptoms. By limiting spread within households, the overall burden of the disease is reduced. The application of phages as prophylactic treatments for mucosal pathogens represents a fast and specific means by which to restrict the impact of bacterial infections on human health.

Example 17. Analysis of *V. cholerae* Biofilms in Fresh Water Response to Phage

Each of the three *V. cholerae* stool isolates, previously obtained by multiple rounds of colony purification, and confirmed to lack phage by plaque assay and genome sequencing, is grown as a biofilm in pond water containing chitin flakes. This process prepares the bacteria in their natural hyperinfectious state within biofilms. The resulting biofilms are turned into single cell suspensions by ultrasonic disruption as described (Tamayo et al. *Infect Immun.* 78(8): 3560-9 (2010). PMCID: PMC2916270).

Lytic phage are added at low multiplicities of infection (MOI) of 0.01, 0.1 and 1. Each mixture is inoculated into groups of nine infant mice by oral gavage as described herein (Nelson et al. *PLoS ICP-2*. 4, e1000187 (2008). PMCID: PMC2563029). These MOIs are physiological in that they cover the typical range found in rice-water stools (Nelson et al. *PLoS ICP-2*. 4, e1000187 (2008); Seed et al. *mBio*. 2(1). pii: e00334-10 (2011). PMCID: PMC3037004). Moreover, each of these MOIs allows a portion of uninfected *V. cholerae* cells to enter the small intestine and establish colonization. A control inoculation without phage is performed for each strain. At 8, 16 and 24 h, three mice per group are euthanized and the titers of phage and *V. cholerae* in the small intestine are determined. Typically, in the absence of phage, an inoculum of $10^5$ CFU of *V. cholerae* increases to greater than $10^7$ CFU by 24 h. Highly virulent phage dramatically increases its own titer through rounds of lytic growth in the bacteria, causing the titer of *V. cholerae* to drop precipitously. In contrast, a less virulent phage has little or no impact on the load of *V. cholerae*. It is found that most or all of the lytic phages tested interfere with *V. cholerae* infection. By monitoring the number of phage present during the course of the infection, whether the effect is through predation and phage replication, or due to a single round phage infection that somehow alters the outcome of *V. cholerae* infection of the animal, is determined.

It is envisioned that, if a lytic phage strongly interferes with *V. cholerae* infection, then there is selective pressure for phage resistance. Populations of *V. cholerae* rapidly become resistant to ICP-1 in vitro through phase-variable loss of LPS O1-antigen production (Seed et al. *PLoS ICP*-2. 8(9): e1002917 (2012). PMCID: PMC3441752). However, these phase variants were found to be avirulent in the infant mouse model of colonization. Accordingly, these phase variants were not detected after screening several hundred colonies from several rice-water stools. Nevertheless, it is possible that such mutants are present at a lower frequency. Because ICP-2 does not use the O1-antigen as a receptor, it is plausible that phage resistance may arise rapidly during intestinal infection, which could have a major impact on phage/*V. cholerae* population dynamics. The archived phage-positive rice-water stool samples are advantageously used to perform a deep screen for phage-resistant isolates.

Samples from about four patients are plated on large petri plates containing medium selective for *V. cholerae*. A robot is programmed to pick 7,680 colonies from each sample into twenty 384-well plates with 60 μl LB broth per well. Each well receives about $10^5$ CFU *V. cholerae*. The media in the wells, except for the first column, contain about $10^3$ plaque-forming units (PFU) of phage, giving a starting MOI of 0.01. The first column of wells contains controls without phage as a positive control for cell growth. The 384-well plates are incubated at 24° C. for 8 h in a plate reader with occasionally shaking, and $OD_{600}$ measurements are made every 0.5 h.

For assaying phage resistance, the $OD_{600}$ is monitored as a function of time, instead of an end-point reading, to obtain information on possible different classes of phage-resistant mutants. From the data, the percentage of phage-resistant isolates is calculated in each stool sample. Phage-resistant isolates are obtained for each stool sample by triple colony-purifying, and are retested for phage resistance as above.

The mechanism(s) of phage resistance is determined through genome sequencing and mutational analysis. The genomes of confirmed phage-resistant isolates from above (up to 72 strains) are sequenced, and are each compared to the phage-sensitive genome isolated from the same stool sample to identify mutations responsible for phage resistance. Candidate phage-resistance mutations are confirmed by transferring the mutations into a fresh cellular background and testing for phage resistance. This strategy is used it to discover phage receptors and novel mechanisms of phage resistance (Seed et al. *mBio*. 2(1). pii: e00334-10, 2011. PMCID: PMC3037004; Seed et al. *Nature*. 494 (7438):489-91, 2013. PMCID: PMC3587790; Seed et al. *PLoS ICP*-2. 8(9):e1002917, 2012. PMCID: PMC3441752).

The examples above provide quantitative information on the population dynamics of lytic phage and *V. cholerae* during intestinal infection, as well as mechanisms of phage-resistance. The results impact understanding of the frequency of association of particular phage stains with *V. cholerae* during outbreaks, and the effect of lytic phage on the outcome of individual infections. In addition, results may serve for developing phage therapies to treat cholera patients.

The population dynamics of clinically obtained pairs of phage strains and *V. cholerae* strains during dissemination are determined. The impact of lytic phage in cholera stools on dissemination of *V. cholerae* is largely unknown. Since productive phage infection requires a metabolically active host, it is here envisioned that phage have a minimal impact on dissemination in nutrient poor water, but a major impact when chitin is present to support growth of *V. cholerae*. Chitin is the major carbon source in natural fresh water environments. In this section, the three lytic phage/*V. cholerae* pairs above are used above to test this hypothesis, using the infant rabbit host and collecting highly disseminative *V. cholerae* and phage from the cecum.

Lytic phage are mixed with biofilm-grown *V. cholerae* as above, and then inoculated orogastrically into groups of three infant rabbits. A control group inoculated without phage is included for each strain. When symptomatic, each animal is euthanized and cecal fluid is collected. The unprocessed sample (no removal of debris or aggregates) is divided and used in the following assays. A portion is vortexed to disperse aggregates and is used to determine the number of phage PFU and *V. cholerae* cells in the sample. Another portion is diluted in pond water with or without added chitin flakes in open beakers to perform dissemination fitness assays. Yet another portion is used to determine the effect of lytic phage on transmission as described below.

For the dissemination assay, phage and *V. cholerae* are assayed for titers after 8, 16, 24, 48 and 96 h of incubation in each beaker. The rate of decline (or growth) of *V. cholerae* is compared to that of the controls lacking phage. The results of these examples shed light on the impact that lytic phage have on the fitness of *V. cholerae* during dissemination in both nutrient-poor and nutrient-sufficient (chitin) environments. If the phage continue to infect and multiply on the shed bacteria in the chitin-containing environment, the life cycle of *V. cholerae* is elucidated. Such data support the concept of controlling bacterial content of environmental reservoirs using lytic phages. On the other hand, given the stress of dissemination, phage may be unable to multiply in either environment, due to nutrient-poor or to chitin-containing environments. In this scenario, phage may still associate with *V. cholerae*, and in this way, remain present and inactive until *V. cholerae* is transmitted to a new host.

Transmissibility of *V. cholerae* that have disseminated in the presence of lytic phage is determined. Despite its importance for understanding the spread of cholera, the effects of lytic phage on fecal-oral transmission of cholera via a pond water intermediate have never been explored. It is envisioned that phage, whether actively replicating or not, but associated with *V. cholerae*, reduce transmission of disease from contaminated water.

The dissemination cultures of cecal fluid *V. cholerae* and associated lytic phage above are used to measure transmission to infant mice with the following modification. Instead of performing competition experiments, the $ID_{50}$ of *V. cholerae* is determined. Competition experiments are not possible here because the lytic phage attack the competing LacZ⁻ *V. cholerae* strain and thus the competitive index (CI) values would be highly variable.

To determine the $ID_{50}$, a portion of the dissemination culture at the 24 h time point from examples above is serially diluted in pond water to achieve a range of concentrations of phage and bacteria. Groups of three infant mice are inoculated orogastrically with dilutions estimated to contain each of $10^1$, $10^2$, $10^3$ and $10^4$ CFU of *V. cholerae*. After 24 h, the infant mice are euthanized and the load of *V. cholerae* in the small intestine is determined. The $ID_{50}$ is determined graphically. This example determines that lytic phage in the pond water reduces the infectivity of *V. cholerae*, i.e., resulting in a substantially higher $ID_{50}$. The results of these examples yield valuable information for understanding the effects of lytic phage on transmission of *V. cholerae* from contaminated bodies of fresh water.

The impact of lytic phage on rapid transmission of cholera is determined. Examples above test the effect of lytic phage on transmission from contaminated pond water. However, an equally important but unanswered question is whether lytic phage impact rapid transmission of hyperinfectious *V. cholerae* shed in rice-water stools. It is envisioned that lytic phage greatly reduces transmission of hyperinfectious stool *V. cholerae*.

The model of hyperinfectious transmission from infant rabbit cecal fluid to infant mice, described above is used to measure transmission for the three phage/*V. cholerae* pairs. The $ID_{50}$ in infant mice is measured for each freshly obtained cecal fluid sample. Using this assay, the $ID_{50}$ of hyperinfectious *V. cholerae* was found to be $10^2$ CFU, which is 10-fold lower than for in vitro grown (non-hyperinfectious) bacteria (Butler et al. *Mol Microbiol* 60 (2), 417-26, 2006. PMCID: PMC2754204; Nelson et al. *PLoS ICP*-2. 4, e1000187, 2008. PMCID: PMC2563029). The $ID_{50}$ for phage-containing samples is accordingly compared to that of samples lacking phage. This example depends on whether lytic phage in the cecal fluid greatly reduces the infectivity of what are normally hyperinfectious *V. cholerae*. The results of these examples yield valuable information for understanding the effects of lytic phage on rapid transmission of stool-shed *V. cholerae*, for example, occurring within households during epidemics (Harris et al. *PLoS Negl. Trop. Dis.* 2,e221, 2008; Weil et al. *Clin Infect Dis.* 15;49(10):1473-9, 2009).

The invention now having been fully described and enabled, further embodiments are described by the following claims, which are exemplary only and are not to be construed as further limiting. The contents of all cited references are hereby incorporated herein in their entireties.

We claim:

1. A composition for preventing or reducing a *Vibrio cholerae* bacterial infection in a human subject, the composition comprising:
    a prophylactic mixture comprising:
    a strain of virulent lytic bacteriophage ICP-1 that infects and lyses cells of the *Vibrio cholerae* bacterial infection;
    a strain of virulent lytic bacteriophage ICP-2 that infects and lyses cells of the *Vibrio cholerae* bacterial infection; and
    a strain of virulent lytic bacteriophage ICP-3 that infects and lyses cells of the *Vibrio cholerae* bacterial infection.

2. The composition according to claim 1, wherein at least one of the strains is a mutant of a wild type bacteriophage, the mutant selected from the group of spontaneous mutants, induced mutants, and genetically engineered recombinants.

3. The composition according to claim 1, further comprising at least one therapeutic agent selected from the group of: an antibiotic, an antifungal, an anti-protozoan, an anti-inflammatory, an anti-dehydration, and a hydrating agent.

4. A method of preventing or reducing a *Vibrio cholerae* bacterial infection in a human subject, the method comprising:
    administering to the subject an effective amount of a composition comprising a prophylactic mixture comprising:
    a strain of virulent lytic bacteriophage ICP-1 that infects and lyses cells of the *Vibrio cholerae* bacterial infection;
    a strain of virulent lytic bacteriophage ICP-2 that infects and lyses cells of the *Vibrio cholerae* bacterial infection; and
    a strain of virulent lytic bacteriophage ICP-3 that infects and lyses cells of the *Vibrio cholerae* bacterial infection.

5. The method according to claim 4 wherein the subject is selected from the group consisting of a household member or a family member of a patient, a doctor, a nurse, a medical worker, and an orderly.

6. The method according to claim 4, wherein the administering step is oral, and the method further comprises, prior to administering, preparing the composition in a formulation as a liquid, a tablet, a capsule, a food additive, or an encapsulated lyophil.

7. The method according to claim 4, wherein administering to the subject is performed prior to exposure to the *Vibrio cholerae* and the method comprises preventing or reducing infection.

8. The method according to claim 4, further comprising prior to the administering step, formulating the composition to a bacteriophage total titer of at least about $10^7$ PFU/ml.

9. A kit comprising a composition for preventing or reducing a *Vibrio cholerae* bacterial infection in a human subject, the composition comprising a prophylactic mixture comprising:
    a strain of virulent lytic bacteriophage strain ICP-1 that infects and lyses cells of the *Vibrio cholerae* bacterial infection;
    a strain of virulent lytic bacteriophage ICP-2 that infects and lyses cells of the *Vibrio cholerae* bacterial infection; and
    a strain of virulent lytic bacteriophage ICP-3 that infects and lyses cells of the *Vibrio cholerae* bacterial infection;
    wherein the composition is in a unit dose.

10. The composition according to claim 1, formulated to a bacteriophage total titer of at least about $10^7$ PFU/ml.

11. The composition according to claim 1, formulated as a liquid, a tablet, a capsule, a food additive, or a lyophil.

12. A pharmaceutical composition comprising the composition according to claim 1 and a pharmaceutically acceptable carrier.

* * * * *